(12) United States Patent
Boyd et al.

(10) Patent No.: US 9,498,410 B2
(45) Date of Patent: *Nov. 22, 2016

(54) ORAL AND PERSONAL CARE COMPOSITIONS AND METHODS

(75) Inventors: Thomas J. Boyd, Metuchen, NJ (US); Guofeng Xu, Princeton, NJ (US); M. Teresa R. Carale, Houston, TX (US); Beth Ann Boff, Piscataway, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 1204 days.

This patent is subject to a terminal disclaimer.

(21) Appl. No.: 11/963,292

(22) Filed: Dec. 21, 2007

(65) Prior Publication Data

US 2008/0160056 A1  Jul. 3, 2008

Related U.S. Application Data

(60) Division of application No. 10/720,462, filed on Nov. 24, 2003, now Pat. No. 7,763,235, which is a continuation of application No. 10/331,312, filed on Dec. 30, 2002, now Pat. No. 6,669,929, application No. 11/963,292, which is a continuation of application No. 10/739,803, filed on Dec. 18, 2003, now abandoned, which is a continuation-in-part of application No. 10/331,312, filed on Dec. 30, 2002, now Pat. No. 6,669,929.

(51) Int. Cl.
| | |
|---|---|
| *A61Q 11/00* | (2006.01) |
| *A61K 8/00* | (2006.01) |
| *A61K 8/02* | (2006.01) |
| *A61K 8/04* | (2006.01) |
| *A61K 8/73* | (2006.01) |

(52) U.S. Cl.
CPC .......... *A61K 8/0283* (2013.01); *A61K 8/0266* (2013.01); *A61K 8/042* (2013.01); *A61K 8/731* (2013.01); *A61K 8/732* (2013.01); *A61Q 11/00* (2013.01); *A61K 2800/262* (2013.01); *A61K 2800/594* (2013.01); *A61K 2800/621* (2013.01); *A61K 2800/651* (2013.01)

(58) Field of Classification Search
USPC ..................... 424/49, 58, 401, 494
See application file for complete search history.

(56) References Cited

U.S. PATENT DOCUMENTS

| 124,902 A | 3/1872 | Lounsbery |
|---|---|---|
| 309,209 A | 12/1884 | Driscoll |
| 446,491 A | 2/1891 | Weston |
| 449,457 A | 3/1891 | Yeo |
| 502,144 A | 7/1893 | Scoular |
| 919,736 A | 4/1909 | Loesch |
| 982,946 A | 1/1911 | Gardner |
| 1,059,162 A | 4/1913 | Janik |
| 1,321,514 A | 11/1919 | Erickson |
| 1,429,405 A | 9/1922 | Carter et al. |
| 1,605,903 A | 11/1926 | Schuler |
| 1,785,078 A | 12/1930 | Gibson |
| 1,947,124 A | 2/1934 | Clauss |
| 2,062,867 A | 12/1936 | Cosier |
| 2,137,170 A | 11/1938 | Levey |
| 2,353,594 A | 7/1944 | Seagren |
| 2,394,322 A | 2/1946 | McKee |
| 2,503,280 A | 4/1950 | Lockwood |
| 2,507,088 A | 5/1950 | Bradley |
| 2,526,811 A | 10/1950 | Dawson |
| 2,610,588 A | 9/1952 | Seagren et al. |
| 2,624,277 A | 1/1953 | Sunkoz |
| 2,645,049 A | 7/1953 | Brown |
| 2,791,960 A | 5/1957 | Pietropinto |
| 2,846,314 A | 8/1958 | Aichele et al. |
| 2,895,832 A | 7/1959 | Bersey |
| 3,009,812 A | 11/1961 | Ganz |
| 3,260,744 A | 7/1966 | Ito et al. |
| 3,320,174 A | 5/1967 | Rubinfeld |
| 3,372,188 A | 3/1968 | Alston et al. |
| 3,711,604 A | 1/1973 | Colodney et al. |
| 3,741,911 A | 6/1973 | Shane |
| 3,852,494 A | 12/1974 | Williamson |
| 3,928,261 A | 12/1975 | Schertler |
| 3,929,988 A | 12/1975 | Barth |
| 3,934,000 A | 1/1976 | Barth |
| 3,944,661 A | 3/1976 | Colodney et al. |
| 3,951,821 A | 4/1976 | Davidson |
| 3,954,961 A | 5/1976 | Colodney et al. |

(Continued)

FOREIGN PATENT DOCUMENTS

| CA | 982943 | 2/1976 |
|---|---|---|
| CA | 982946 | 3/1976 |

(Continued)

OTHER PUBLICATIONS

The Herbarie, http://www.theherbarie.com/Hydroxypropyl-Methycellulose-HPMC-pr-230.html, retrieved Feb. 24, 2012, pp. 1-2.*

Basf The Chemical Company, 2009, Kollicoat® SR 30 D Poly (Yinyl Acetate) Dispersion 30 Per Cent Ph. Fur. Technical Information.

Dow, 1999, "A Formulator's Guide to Methocel Cellulose Ethers in Personal Care Products".

(Continued)

*Primary Examiner* — Lezah Roberts

(57) ABSTRACT

A dentifrice composition comprising an orally acceptable vehicle having distributed therein a water hydratable film flakes having a matrix comprised of a water soluble hydroxy alkyl cellulose polymer and a starch, and having entrained therein a constituent selected from therapeutic cosmetic and decorative materials.

6 Claims, No Drawings

(56) References Cited

U.S. PATENT DOCUMENTS

| | | |
|---|---|---|
| 3,957,964 A | 5/1976 | Grimm, III |
| 3,957,968 A | 5/1976 | Cordon |
| 4,003,971 A | 1/1977 | Mannara |
| 4,048,299 A | 9/1977 | Litchfield et al. |
| 4,075,316 A | 2/1978 | Cordon |
| 4,089,943 A | 5/1978 | Roberts et al. |
| 4,129,520 A | 12/1978 | Peterson |
| 4,136,162 A | 1/1979 | Fuchs et al. |
| 4,185,106 A | 1/1980 | Dittmar et al. |
| 4,209,417 A | 6/1980 | Whyte |
| 4,285,978 A | 8/1981 | Quinlivan |
| 4,376,762 A | 3/1983 | Hauschild et al. |
| 4,440,877 A * | 4/1984 | Hauschild et al. ............ 523/105 |
| 4,470,982 A | 9/1984 | Winkler |
| 4,597,959 A | 7/1986 | Barr |
| 4,642,197 A | 2/1987 | Kruse et al. |
| 4,650,685 A | 3/1987 | Persson et al. |
| 4,820,506 A | 4/1989 | Kleinberg et al. |
| 4,837,008 A | 6/1989 | Rudy et al. |
| 4,839,157 A | 6/1989 | Mei-King Ng et al. |
| 4,849,212 A | 7/1989 | Glandorf et al. |
| RE33,093 E | 10/1989 | Schiraldi et al. |
| 4,876,092 A | 10/1989 | Mizobuchi et al. |
| 4,897,258 A | 1/1990 | Rudy et al. |
| 4,950,479 A | 8/1990 | Hill et al. |
| 4,956,404 A | 9/1990 | Pelzig |
| 4,971,782 A | 11/1990 | Rudy et al. |
| 5,017,394 A | 5/1991 | Macpherson et al. |
| 5,035,906 A | 7/1991 | Persson et al. |
| 5,045,305 A | 9/1991 | Clarkson et al. |
| 5,047,244 A | 9/1991 | Sanvordeker et al. |
| 5,062,986 A | 11/1991 | Fujita et al. |
| 5,071,704 A | 12/1991 | Fischel-Ghodsian |
| 5,089,269 A | 2/1992 | Noda et al. |
| 5,145,668 A | 9/1992 | Chow et al. |
| 5,185,106 A | 2/1993 | Chen et al. |
| 5,242,615 A | 9/1993 | Urfer et al. |
| 5,266,306 A | 11/1993 | Ohtsuki et al. |
| 5,354,551 A | 10/1994 | Schmidt |
| 5,425,953 A | 6/1995 | Sintov et al. |
| 5,447,584 A | 9/1995 | Shakespeare et al. |
| 5,455,043 A | 10/1995 | Fischel-Ghodsian |
| 5,538,663 A | 7/1996 | Kihara et al. |
| 5,616,315 A | 4/1997 | Masterman et al. |
| 5,643,603 A | 7/1997 | Bottenberg et al. |
| 5,695,746 A | 12/1997 | Garlick, Jr. |
| 5,700,449 A | 12/1997 | Katayama et al. |
| 5,700,478 A | 12/1997 | Biegajski et al. |
| 5,711,943 A | 1/1998 | Grossman |
| 5,792,446 A | 8/1998 | Ashley |
| 5,843,415 A | 12/1998 | Klar |
| 5,866,531 A | 2/1999 | Assmann et al. |
| 5,869,029 A | 2/1999 | Graff-Andersen et al. |
| 5,869,437 A | 2/1999 | Wolfersberger |
| 5,900,399 A | 5/1999 | Seiter et al. |
| 5,910,472 A | 6/1999 | Elliott et al. |
| 5,931,999 A | 8/1999 | Aisner |
| 5,939,093 A | 8/1999 | Park et al. |
| 5,948,430 A | 9/1999 | Zerbe et al. |
| 5,958,525 A | 9/1999 | Green et al. |
| 5,990,058 A | 11/1999 | Bac et al. |
| 5,990,205 A | 11/1999 | Cordova |
| 6,007,795 A | 12/1999 | Masterman et al. |
| 6,051,059 A | 4/2000 | Aisner |
| 6,117,419 A | 9/2000 | Vernice |
| 6,138,315 A | 10/2000 | Schmitt et al. |
| 6,210,699 B1 | 4/2001 | Acharya et al. |
| 6,221,832 B1 | 4/2001 | Casteel et al. |
| 6,232,285 B1 | 5/2001 | Casteel et al. |
| 6,241,974 B1 | 6/2001 | White, Jr. et al. |
| 6,251,452 B1 | 6/2001 | Weinstein et al. |
| 6,258,342 B1 | 7/2001 | Harcum et al. |
| 6,258,343 B1 | 7/2001 | Kiczek, Sr. et al. |
| 6,294,509 B1 | 9/2001 | Meiwa et al. |
| 6,315,986 B1 | 11/2001 | Wong et al. |
| 6,352,701 B1 | 3/2002 | Scholz et al. |
| 6,365,209 B2 | 4/2002 | Cherukuri |
| 6,379,654 B1 | 4/2002 | Gebreselassie et al. |
| 6,403,543 B1 | 6/2002 | George |
| 6,419,903 B1 | 7/2002 | Xu et al. |
| 6,447,761 B1 | 9/2002 | Ramin |
| 6,451,754 B1 | 9/2002 | Rowland et al. |
| 6,492,320 B2 | 12/2002 | Guo et al. |
| 6,497,899 B2 | 12/2002 | Thombre et al. |
| 6,503,495 B1 | 1/2003 | Alwattari et al. |
| 6,506,720 B1 | 1/2003 | Blasey et al. |
| 6,509,007 B2 | 1/2003 | Rajaiah et al. |
| 6,524,562 B2 | 2/2003 | Guskey |
| 6,531,119 B1 | 3/2003 | Hall-Puzzio et al. |
| 6,541,441 B2 | 4/2003 | Mumoli |
| 6,544,943 B1 | 4/2003 | Ricci et al. |
| 6,548,473 B1 | 4/2003 | Jacques Kamiel Thoen et al. |
| 6,569,261 B1 | 5/2003 | Aubay et al. |
| 6,576,225 B1 | 6/2003 | Kilcher |
| 6,585,997 B2 | 7/2003 | Moro et al. |
| 6,586,013 B2 | 7/2003 | Victor |
| 6,589,924 B2 | 7/2003 | Schmidt et al. |
| 6,596,298 B2 | 7/2003 | Leung et al. |
| 6,620,777 B2 | 9/2003 | Heibel et al. |
| 6,635,702 B1 | 10/2003 | Schmucker-Castner |
| 6,638,521 B2 | 10/2003 | Dobrozsi |
| 6,664,217 B1 | 12/2003 | Puvvada et al. |
| 6,664,225 B2 | 12/2003 | Mumoli |
| 6,669,929 B1 | 12/2003 | Boyd et al. |
| 6,682,756 B1 | 1/2004 | Horstmann et al. |
| 6,706,675 B1 | 3/2004 | Demson et al. |
| 6,797,683 B2 | 9/2004 | Shana'a et al. |
| 6,957,964 B2 | 10/2005 | Chiang |
| 7,025,983 B2 | 4/2006 | Leung et al. |
| 7,049,274 B2 | 5/2006 | Ranade et al. |
| 7,132,113 B2 | 11/2006 | Zerbe et al. |
| 7,181,588 B2 | 2/2007 | Johnson |
| 7,323,162 B2 | 1/2008 | Martin et al. |
| 7,410,649 B2 | 8/2008 | Yoshimi et al. |
| 2001/0022964 A1 | 9/2001 | Leung et al. |
| 2001/0048965 A1* | 12/2001 | Cherukuri ................... 426/660 |
| 2002/0001569 A1 | 1/2002 | Dromard et al. |
| 2002/0034542 A1 | 3/2002 | Thombre |
| 2002/0048553 A1 | 4/2002 | Baumgartner |
| 2002/0051797 A1 | 5/2002 | Jezior |
| 2002/0064541 A1 | 5/2002 | Lapidot et al. |
| 2002/0110536 A1 | 8/2002 | Osumi |
| 2002/0169270 A1 | 11/2002 | Amberg-Schwab |
| 2002/0187108 A1 | 12/2002 | Rajaiah et al. |
| 2003/0008144 A1 | 1/2003 | Whitney et al. |
| 2003/0053962 A1* | 3/2003 | Zerbe et al. ................... 424/49 |
| 2003/0171232 A1 | 9/2003 | Freeman et al. |
| 2004/0086468 A1 | 5/2004 | Prosise |
| 2004/0126332 A1 | 7/2004 | Boyd et al. |
| 2004/0136924 A1 | 7/2004 | Boyd |
| 2004/0219119 A1 | 11/2004 | Wei |
| 2004/0236924 A1 | 11/2004 | Johnson et al. |
| 2005/0019273 A1 | 1/2005 | Boyd |
| 2005/0043209 A1 | 2/2005 | Schmiedel et al. |
| 2005/0106112 A1 | 5/2005 | Boyd |
| 2005/0281757 A1 | 12/2005 | Ibrahim et al. |
| 2006/0018845 A1 | 1/2006 | Edelstein et al. |
| 2006/0189503 A1 | 8/2006 | Gambogi et al. |
| 2006/0292088 A1 | 12/2006 | Maitra et al. |
| 2007/0010415 A1 | 1/2007 | Kinscherf et al. |
| 2007/0066507 A1 | 3/2007 | Fleckenstein et al. |
| 2007/0148213 A1 | 6/2007 | Ibrahim et al. |
| 2007/0196313 A1 | 8/2007 | Scala et al. |
| 2008/0014393 A1 | 1/2008 | Denome et al. |
| 2008/0024281 A1 | 1/2008 | Shimura |
| 2008/0138369 A1 | 6/2008 | Boyd et al. |

FOREIGN PATENT DOCUMENTS

| | | |
|---|---|---|
| CA | 2512159 | 7/2004 |
| CA | 2548386 | 6/2005 |
| CN | 1303259 | 7/2001 |
| CN | 1422147 | 6/2003 |
| DE | 735096 | 5/1943 |

(56) References Cited

FOREIGN PATENT DOCUMENTS

| | | |
|---|---|---|
| DE | 103 52 845 A1 | 6/2005 |
| EP | 0 449 457 B1 | 10/1991 |
| EP | 0 499 457 B1 | 10/1991 |
| EP | 0711544 | 5/1996 |
| EP | 1 051 962 B1 | 11/2000 |
| EP | 1059162 | 12/2000 |
| EP | 1 153 594 A2 | 11/2001 |
| EP | 1 321 514 | 6/2003 |
| EP | 1319706 | 6/2003 |
| FR | 446491 | 12/1912 |
| GB | 446 491 | 4/1936 |
| GB | 1 309 209 | 3/1973 |
| GB | 1465190 | 2/1977 |
| GB | 1 502 144 | 2/1978 |
| GB | 1502144 | 2/1978 |
| GB | 2 124 902 A | 2/1984 |
| JP | 58-216109 | 12/1983 |
| RU | 2000116843 | 10/2002 |
| WO | WO 98/20862 | 5/1998 |
| WO | 9922710 A1 | 5/1999 |
| WO | WO 99/36478 | 7/1999 |
| WO | WO 00/06089 | 2/2000 |
| WO | 0018365 A2 | 4/2000 |
| WO | WO 00/42992 | 7/2000 |
| WO | 0117488 A1 | 3/2001 |
| WO | 0180823 A2 | 11/2001 |
| WO | WO 01/80821 | 11/2001 |
| WO | WO 01/80832 | 11/2001 |
| WO | 0202128 A2 | 1/2002 |
| WO | WO 02/02128 | 1/2002 |
| WO | WO 02/041765 | 9/2002 |
| WO | WO 02/092028 | 11/2002 |
| WO | WO 03/030881 | 4/2003 |
| WO | 03034979 A2 | 5/2003 |
| WO | WO 2004/006967 | 1/2004 |
| WO | WO 2004/020566 | 3/2004 |
| WO | 2004060335 A1 | 7/2004 |
| WO | WO 2004/060290 | 7/2004 |
| WO | 2005110344 A1 | 11/2005 |
| WO | 2006013081 A1 | 2/2006 |
| WO | WO 2006/089057 | 8/2006 |
| WO | WO 2007/022229 | 2/2007 |
| WO | WO 2007/130684 | 11/2007 |

OTHER PUBLICATIONS

Dow, 2010, METHOCEL™ Products, Dow Excipients http://www.dow.com/dowexcipients/products/methocel.htm, accessed Apr. 8, 2010.
Grain Processing Corp.'s "Instant Pure-Cote® B793 Modified Starch," Product Bulletin undated.
International Search Report and Written Opinion International Application No. PCT/US03/040562, mailed Sep. 30, 2004.
International Search Report and Written Opinion in International Application No. PCT/US04/042442, mailed Mar. 29, 2005.
International Search Report and Written Opinion in International Application No. PCT/US06/031922, mailed Dec. 6, 2006.
International Search Report and Written Opinion International Application No. PCT/US06/062539, mailed Jun. 20, 2007.
International Search Report and Written Opinion in International Application No. PCT/US10/031717, mailed Aug. 18, 2010.
International Search Report and Written Opinion in International Application No. PCT/US10/032189, mailed Aug. 17, 2010.
McClelland, 1997, "Defining Colors," MacWorld PhotoShop 4 Bible, Chapter 5, pp. 157-184.
National Adademy of Sciences, 1965, "Group II: Flavoring Agents, Sub-Group A: Synthetic Flavors," Chemicals Used in Food Processing, Publication 1274, pp. 63-258.
Salsa et al., 1997, "Oral Controlled-Release Dosage Forms, I. Cellulose Ether Polymers in Hydrophilic Matrices," Drug Development and Industrial Pharmacy 23(9):929-938.
U.S. Appl. No. 10/720,462 File History to Jun. 3, 2013.
U.S. Appl. No. 11/014,571 File History to Jun. 3, 2013.
U.S. Appl. No. 11/316,626 File History to Jun. 3, 2013.
U.S. Appl. No. 11/465,525 File History to Jun. 3, 2013.
U.S. Appl. No. 11/967,878 File History to Jun. 3, 2013.
American Dental Association (http://www.ada.org/public/topics/bad_breath.asp) pp. 1-2 Dec. 2003.
American Academy of Periodontology http://www.perio.org/consumer/faq_general.htm, pp. 1-4 Oct. 2004.
Your Dictionary.com http://www.yourdictionary.com/and/d/d0136300.html, (2007) p. 1.
European Search Report for Application No. EP09158190 mailed Sep. 1, 2009.

* cited by examiner

ORAL AND PERSONAL CARE COMPOSITIONS AND METHODS

This application is a divisional application of U.S. Ser. No. 10/720,462 filed Nov. 24, 2003 now U.S. Pat. No. 7,763,235 which is a continuation application of U.S. Ser. No. 10/331,312 filed Dec. 30, 2002, now U.S. Pat. No. 6,669,929 B1 and this application is also a continuation of U.S. patent application Ser. No. 10/739,803 filed Dec. 18, 2003, now abandoned which is a continuation-in-part of U.S. patent application Ser. No. 10/331,312 filed Dec. 30, 2002, now U.S. Pat. No. 6,669,929 B1. The disclosures of the above applications are incorporated herein by reference in their entirety.

BACKGROUND OF THE INVENTION

Introduction

This application relates to oral and personal care compositions, and more particularly to compositions comprising a film entrained in a carrier. Such compositions include, for example, dentifrices. Compositions for enhancing health, hygiene or appearance, such as oral care compositions, skin care compositions and hair care compositions, are used by millions of people. These compositions are used for a wide variety of purposes, including for enhancing personal health, hygiene, and appearance, as well as for preventing or treating a variety of diseases and other conditions in humans and in animals.

The formulation of such compositions presents a number of challenges. They must be pharmaceutically and/or cosmetically acceptable for their intended use. Compositions that contain therapeutic active materials preferably deliver the active at effective levels, avoiding undue chemical degradation. Similarly, compositions containing cosmetically functional materials must deliver the material to, e.g. the oral cavity, skin or hair at effective levels under the conditions that they are typically used by the consumer.

Moreover, the aesthetic appeal of all such compositions is important, and can have significant effects on consumer acceptance and usage. Aesthetic effects have been acknowledged to play an important role in consumer acceptance of many products. Although such products have met with consumer approval, the art seeks to further improve the aesthetic effects as well as the cosmetic and therapeutic benefits of these products. Indeed, many such compositions known in the art are deficient in one or more attributes. Thus, there is an ongoing need for new oral and personal care compositions, and methods of their use.

SUMMARY

The present invention provides, in various embodiments, oral and personal care compositions comprising a film entrained in a carrier, wherein said film comprises a functional material. In one embodiment, the film comprises a plurality of film fragments. In various embodiments, the present invention provides compositions comprising a plurality of lamellar fragments in a carrier.

In some embodiments, the film can comprise a polymer, such as a water soluble polymer, water dispersible polymer, a water insoluble polymer or a mixture thereof. In various embodiments, the composition can be suitable for use as an oral care composition, a hair care composition, or a skin care composition. In various embodiments the film comprises a functional material. In various embodiments, such functional materials include therapeutic active materials, flavorants, cosmetic materials, fragrances, and formulation colorants.

The present invention also provides methods for administering a functional material to a human or animal subject in need thereof, comprising topically applying to said subject a composition comprising a film entrained in a carrier, wherein said film comprises said functional material. In various methods, such methods further comprise disrupting the film after the topical application.

Compositions and methods of this invention afford benefits over compositions and methods among those known in the art. Such benefits include one or more of increased consumer acceptability, enhanced aesthetics, improved stability for active or other functional materials, and controlled delivery of functional materials. Further benefits and embodiments of the present invention are apparent from the description set forth herein.

DESCRIPTION

The present invention provides compositions and methods, for administration to, or use with, a human or other animal subject. Preferably, specific materials and compositions to be used in this invention are, accordingly, pharmaceutically- or cosmetically-acceptable. As used herein, such a "pharmaceutically acceptable" or "cosmetically acceptable" component is one that is suitable for use with humans and/or animals to provide the desired therapeutic, sensory, decorative, or cosmetic benefit without undue adverse side effects (such as toxicity, irritation, and allergic response) commensurate with a reasonable benefit/risk ratio. The following definitions and non-limiting guidelines must be considered in reading and interpreting the description of this invention set forth herein.

The headings (such as "Introduction" and "Summary,") and sub-headings (such as "Film" and "Carrier") used herein are intended only for general organization of topics within the disclosure of the invention, and are not intended to limit the disclosure of the invention or any aspect thereof. In particular, subject matter disclosed in the "Introduction" may include aspects of technology within the scope of the invention, and may not constitute a recitation of prior art. Subject matter disclosed in the "Summary" is not an exhaustive or complete disclosure of the entire scope of the invention or any embodiments thereof.

The citation of references herein does not constitute an admission that those references are prior art or have any relevance to the patentability of the invention disclosed herein. All references cited in the Description section of this specification are hereby incorporated by reference in their entirety.

The description and specific examples, while indicating embodiments of the invention, are intended for purposes of illustration only and are not intended to limit the scope of the invention. Recitation of multiple embodiments having stated features is not intended to exclude other embodiments having additional features, or other embodiments incorporating different combinations of the stated features. Specific Examples are provided for illustrative purposes of how to make, use and practice the compositions and methods of this invention and, unless explicitly stated to recite activities that have been done (i.e., using the past tense), are not intended to be a representation that given embodiments of this invention have, or have not, been performed.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention. As used herein, the word "include," and its variants, is intended to be non-limiting, such that recitation of items in a list is not to the exclusion of other like items that may also be useful in the materials, compositions, devices, and methods of this invention.

The present invention provides oral or personal care compositions, comprising a film entrained in a carrier, wherein said film comprises a functional material. As referred to herein, an "oral or personal care composition" is any composition that is suitable for administration or application to a human or animal subject for enhancing the health, hygiene or appearance of the subject, including the prevention or treatment of any physiologic condition or disorder, and providing sensory, decorative or cosmetic benefits and combinations thereof. Compositions among those provided herein include oral care compositions, skin care compositions, hair care composition, topical pharmaceutical compositions, and ocular compositions. By "oral care composition" as used herein is meant a composition for which the intended use can include oral care, oral hygiene, or oral appearance, or for which the intended method of use can comprise administration to the oral cavity. By "skin care composition" as used herein is meant a composition for which the intended use can include promotion or improvement of health, cleanliness, odor, appearance, or attractiveness of skin.

Film:

Embodiments of this invention comprise a film. As referred to herein, a "film" is a material having a substantially lamellar structure. A "lamellar" structure has, or is capable of having, a size in one or two dimensions (e.g. the x- or y-dimensions) that is substantially greater than the thickness of the structure in a third dimension (e.g., the z-direction). Lamellar structures among those useful herein include those that are substantially planar, layered, or lamelliform. In one embodiment, the lamellar structure is substantially planar, having a size in both the x- and y-dimensions that is substantially greater than the z-direction. In other embodiments, the lamellar structure is non-planar. In one embodiment, a film of this intention comprises a substantially continuous surface that can appear as a substantially flat surface, although in some embodiments the film is deformed. In such embodiments, the film can have any of a number of shapes, including having a smooth curved surface.

Films among those useful herein may be rigid or plastic comprising any of a variety of materials, including materials selected from the group consisting of film forming materials, clays, waxes, and mixtures thereof. In one embodiment, the film comprises a film forming polymer. Film forming polymers among those useful herein include materials selected from the group consisting of water soluble polymers, water dispersible polymers, water insoluble polymers, and mixtures thereof.

In some embodiments, a film comprises at least one film forming material. In certain embodiments, a film forming material is a polymer. Polymers useful herein include hydrophilic polymers and hydrophobic polymers. In certain embodiments, the polymer is a water soluble polymer. In some embodiments, the polymer is a water soluble, breakable polymer that dissolves during use, such as, for example, during toothbrushing. The dissolution can occur as a result of, for example, shearing and/or exposure to a solvent comprising a high concentration of water, such as saliva. In some embodiments, the polymer is insoluble but breakable in water by being dispersible, i.e., the polymer breaks down into small fragments, for example, as a result of shearing. In some embodiments, a polymer is insoluble but swellable. In configurations in which a polymer does not break down during use, the polymer can be a water-repellant polymer or an aqueous-stable hydrophilic polymer such as certain types of cellulose, for example paper. In some embodiments, a film fragment can comprise a mixture of film forming materials.

Water soluble polymers among those useful herein include cellulose ethers, methacrylates, polyvinylpyrrolidone, and mixtures thereof. In one embodiment, the polymer is a cellulose ether, including those selected from the group consisting of hydroxyalkyl cellulose polymers such as hydroxypropyl methyl cellulose (HPMC), hydroxypropyl cellulose, hydroxyethyl cellulose, methyl cellulose, carboxymethyl cellulose, and mixtures thereof. Other polymers among those useful herein include polyvinylpyrrolidone, cross-linked polyvinyl pyrrolidone, polyvinylpyrrolidone-vinyl acetate copolymer, polyvinylalcohol, polyacrylic acid, poly acrylate polymer, cross-linked polyacrylate polymer, cross-linked polyacrylic acid (e.g, Carbopol®), polyethylene oxide, polyethylene glycol, poly vinylalkyl ether-maleic acid copolymer (such as Gantrez®) and carboxy vinyl polymer; natural gums such as sodium alginate, carrageenan, xantham gum, gum acacia, arabic gum, guar gum, pullulan, agar, chitin, chitosan, pectin, karaya gum, zein, hordein, gliadin, locust bean gum, tragacantha and other polysaccharides; starches such as maltodextrin, amylose, high amylose starch, corn starch, potato starch, rice starch, tapioca starch, pea starch, sweet potato starch, barley starch, wheat starch, waxy corn starch, modified starch (e.g. hydroxypropylated high amylose starch), dextrin, levan, elsinan and gluten, and proteins such as collagen, whey protein isolate, casein, milk protein, soy protein and gelatin.

Non-limiting examples of water dispersable and swellable polymers include modified starch, alginate esters, divalent or multivalent ion salts of alginates. Non-limiting examples of water insoluble polymers include polymers soluble in at least one organic solvent, such as cellulose acetate, cellulose nitrate, ethylene-vinyl acetate copolymers, vinyl acetate homopolymer, ethyl cellulose, butyl cellulose, isopropyl cellulose, shellac, silicone polymer (e.g. dimethylsilicone), PMMA (poly methyl methacrylate), cellulose acetate phthalate and natural or synthetic rubber; polymers insoluble in organic solvents, such as cellulose, polyethylene, polypropylene, polyesters, polyurethane and nylon.

Films of this invention, in some embodiments, comprise inorganic materials. Such materials including those selected from the group consisting of mica, mica coated with titanium dioxide, clay, mother-of-pearl, and combinations thereof. In some embodiments, the film forming material comprises graphite. In some embodiments, a film forming material comprises a hydrophobic organic non-polymeric material such as a wax, for example bees wax, or a paraffin.

In one embodiment, the film comprises an hydroxyalkyl cellulose such as hydroxypropyl methyl cellulose, hydroxyethylpropyl cellulose, hydroxybutyl methyl cellulose, hydroxy propyl methyl cellulose and carboxymethyl cellulose. Preferably in one such embodiment, the cellulose polymer is a low viscosity HPMC. When HPMC is used as the film forming agent it is preferred that the HPMC have a viscosity in the range of about 1 to about 1000 millipascal seconds (mPa·s) as determined as a 2% by weight aqueous solution of the HPMC at 20° C. using a Ubbelohde tube viscometer. Preferably the HPMC has a viscosity of about 3 to about 500 mPa·s at 20° C. HPMC is available commercially, for example, from the Dow Chemical Company under the trade designation Methocel, including, for example, Methocel E5LV, Methocel E50, and Methocel K100. Methocel E5 LV is a USP grade, low viscosity HPMC having 29.1% methoxyl groups and 9% hydroxyproxyl group substitution. It is a white or off-white free-flowing dry powder. As a 2 wt. % solution in water as measured with a Ubbelohde tube viscometer it has a viscosity of 5.1 mPa·s at 20° C. In one embodiment, the hydroxyalkyl methyl cellulose is incorporated in the film matrix in amounts ranging from about 10 to about 80% by weight and preferably about 30 to about 60% by weight.

In various embodiments, the compositions of the present invention comprise a plurality of lamellar fragments entrained in a carrier. In one embodiment, the composition comprises a film, wherein the film comprises lamellar fragments of the film material. In one embodiment, the composition comprises a carrier having distributed therein a plurality of lamellar fragments, wherein said fragments comprise a matrix and a functional material. In one such embodiment, the matrix comprises a film. Such fragments may be of any of a variety of shapes or forms, including semi-solid or solid discrete portions, fragments, particles, flakes, or combinations thereof. In various embodiments, the film comprises a first plurality of fragments and a second plurality of fragments, wherein the first plurality of fragments differ in composition or appearance from the second plurality of fragments. Such difference in composition or appearance can be in any aspect of the composition of the fragment (e.g., different film components, different functional material, different formulation colorant), different appearance (e.g., shape, color, texture, refractive index, reflective index), or combinations thereof.

In various embodiments, the fragments exhibit perceivable contrast with the carrier. The perceivable contrast can be sensory contrast, such as optical contrast, tactile contrast, taste contrast, or olfactory contrast. In some configurations, optical contrast can be color contrast, or a difference in refractive index or reflective index. In some configurations, color contrast can be imparted by one or more colorants that comprise different components of the composition. In various embodiments, the present invention provides compositions comprising a plurality of film fragments in a carrier, wherein said fragments are visibly discernable. As referred to herein, "visibly discernable" refers to one or more characteristics of a fragment which cause the fragment to have a different physical appearance, preferably to the naked eye, relative to the carrier in which the fragment is entrained. Such characteristics include color, opacity, refractive index, reflective index, size, shape, and combinations thereof.

In various embodiments, the fragments have a non-random shape. In one embodiment, a "non-random" shape is a shape which results from a manufacturing process of shaping, cutting, or other forming process by which a specific shape is imparted to a fragment. In such embodiments, a non-random shape is distinguished from such shapes that result from simple precipitation or grinding of a material. In one embodiment, a "non-random" shape is "repeating," wherein the composition comprises a plurality of fragments have substantially the same shape. Such repeating shape may have any of a variety of forms, and may be selected based on a variety of aesthetic or functional criteria. In certain embodiments, the shape of a film fragment can be a recognizable shape. In certain embodiments, a film fragment can comprise a nonrandom shape. Such shapes include simple geometric shapes, such as polygons and elliptical shapes, such as triangles, quadrilaterals (such as a square, a rectangle, a rhombus), pentagons, hexagons, oval, and circles. In one embodiment, the repeating shape is a square. Repeating shapes include, in other embodiments, shapes that are representative of figures or animate or inanimate objects, such as stars, hearts, gems, flowers, trees, shamrocks, a letter of an alphabet, numbers, animals, people, and faces. In various embodiments, the composition comprises a single repeating shape. In other embodiments, the composition comprises a plurality of fragments having a plurality of repeating shapes. In one embodiment, the compositions of the present invention comprise a plurality of first film fragments having a first repeated shape and a plurality of second film fragments having a second repeated shape, wherein the first repeated shape is different from the second repeated shape.

In various embodiments, the size of the fragments is not critical, and may be determined pursuant to any of a variety of criteria, including manufacturing convenience, affect on visual appearance, surface area, affect on texture in the composition, and combinations thereof. In some embodiments, the film fragments can be up to about 1 inch (25.4 mm) in length in the longest dimension. As referred to herein, "long dimension" is the dimension of a fragment in length or width (i.e., in the x- and y-dimensions, as the fragment is, or is deformed to be, in a planar shape) in a dimension substantially perpendicular to the "thickness" or shortest dimension of the fragment (i.e., the z-dimension). It is understood that in various embodiments comprising a plurality of fragments, the fragments may be present in a range of sizes due to a variety of factors, including random variation in size, manufacturing tolerances, and intentional sizing or mixing of the fragments through sieving or similar means. As referred to herein, sizes refer to the average size of fragments in a given plurality of fragments.

In various embodiments, the fragments are from about 0.2 mm to about 15 mm in long dimension. In various embodiments, the long dimension of the fragments is from 0.2 mm to about 10 mm, from about 0.5 mm to about 10 mm, from about 0.9 mm to about 5 mm, or from about 1.5 mm to about 2.5 mm. In some embodiments, the long dimension of the fragments is at least about 3 mm, and can be from about 6 mm to about 13 mm. In certain embodiments, a plurality of film fragments are greater than about 600 microns in the longest dimension. In certain embodiments, a plurality of film fragments are greater than about 1 millimeter in the longest dimension.

In one embodiment, wherein the fragment comprises mother-of-pearl, the fragments are greater than about 590 microns in their longest dimension. In one embodiment, wherein the fragment comprises mica film fragments coated with a thin layer of titanium dioxide, the film fragments are greater than 110 microns in their longest dimension.

In various embodiments, the fragments of the present invention have a thickness of from about 1 mil (thousandth of an inch, 25.4 microns) to about 3 mils (76.2 microns). In various embodiments, the fragments have a thickness of from about 0.1 mils (2.54 microns) up to about 10 mils (254 microns), of from about 0.5 mils (12.7 microns) up to about 5 mils (127 microns), or from about 1.4 mils (35.6 microns) to about 2.0 mils (50.8 microns).

In some embodiments, the compositions of the present invention comprise fragments having an aspect ratio of at least about 5:1. As referred to herein, "aspect ratio" of a fragment is the ratio of the diameter of the smallest imaginary sphere that can enclose the object to the diameter of the largest imaginary sphere that can be completely inside the object and tangent to the surfaces of the object. For example, the aspect ratio of a sphere is 1:1; in another example, the aspect ratio of a cylinder that is 2 inches (50.8 mm) long and ¼ inch (6.35 mm) in diameter is slightly over 8:1; in yet another example, a film fragment of the present invention that is 1 mil (25.4 microns) in thickness, 1 inch (25.4 mm) in length, and 1 inch (25.4 mm) wide has an aspect ratio of about 1414:1.

In some embodiments, the compositions of the present invention comprise fragments having an aspect ratio of at least about 10:1. In various embodiments, the fragments have an aspect ratio of from about 5:1 to about 10,000:1, from about 10:1 to about 1,000:1, or from about 20:1 to about 100:1, or from about 25:1 to about 35:1.

In various embodiments, the film comprises a formulation colorant, that imparts a color to the film, the composition, or both. In various embodiments, the film fragments contrast with the carrier, and are white, black, or of any color that is visible against or contrasts with the carrier background. Formulation colorants among those useful herein include non-toxic water soluble dyes or pigment, such as, for example, metallic oxide "lakes." In certain embodiments, the colorant is approved for incorporation into a food or drug by a regulatory agency, such as FD&C or D&C pigments and dyes approved by the FDA for use in the United States. Colorants among those useful herein include FD&C Red No. 3 (sodium salt of tetraiodofluorescein), Food Red 17, disodium salt of 6-hydroxy-5-{(2-methoxy-5-methyl-4-sulphophenyl)azo}-2-naphthalenesulfonic acid. Food Yellow 13, sodium salt of a mixture of the mono and disulphonic acids of quinophthalone or 2-(2-quinolyl) indanedione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphthol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-Δ-3,5-cyclohexadienimine], FD&C Blue No. 1 (disodium salt of dibenzyldiethyl-diaminotriphenylcarbinol trisulfonic acid anhydrite), FD&C Blue No. 2 (sodium salt of disulfonic acid of indigotin), and mixtures thereof in various proportions. In one embodiment, the colorant comprises a water insoluble inorganic pigment, such as titanium dioxide, chromium oxide green, phthalocyanine green, ultramarine blue, ferric oxide, or a water insoluble dye lake. In some embodiments, dye lakes include calcium or aluminum salts of an FD&C dye such as FD&C Green #1 lake, FD&C Blue #2 lake, D&C Red #30 lake or FD&C # Yellow 15 lake. In certain embodiments, a water soluble dye, such as, for example, FD&C Blue #1, is contained within a water-insoluble polymer such as, for example polyethylene such as that found in polyethylene beads (e.g., Microblue Spectrabeads, sold by Micropowders, Inc.). In certain embodiments, the film comprises a dye such as D&C Red #30. In certain embodiments, a white colorant is used, for example titanium dioxide ($TiO_2$), titanium dioxide coated mica (e.g., Timiron), a mineral, or a clay. In certain embodiments, the colorant is a non-bleeding dye. In various embodiments, the film comprises a colorant at a level of from about from 0.5% to about 20% by weight of the film, or from about 1% to about 15% by weight of the film, or from about 3% to about 12% by weight of the film. In one embodiment, the compositions of the present invention comprise a first plurality of film fragments comprising a first color, and a second plurality of film fragments comprising a second color. Preferably, the second color is different than the first color.

In some embodiments, color space coordinates of phases of a composition, such as, for example, a film and a carrier (e.g., toothpaste), can be determined separately. In certain embodiments, the coordinates for a product film/carrier pairing can be quite far apart (such as disclosed in Example 12, infra), and can contribute to a compositions aesthetic appeal, for example by contributing to a striking nature of a composition's aesthetic appeal. In certain alternative embodiments, the coordinates for a product film/carrier pairing can be not particularly large yet still have a noticeable aesthetic effect. In certain embodiments, the L a*b* system established by the Commission Internationale d'Eclairage (CIE) is used to establish color values. (See, for example, McClelland. D., *Macworld® Photoshop® 4 Bible*, IDG Books Worldwide, Inc. 1997, pp. 157-184.) In addition, the quantity $\Delta E^*$ can also be indicative of noticeable color differences. $\Delta E^*$ can be determined using the following equation. $\Delta E^* = \{(\Delta L^*)^2 (\Delta a^*)^2 + (\Delta b^*)^2\}^{1/2}$ where $\Delta L^*$ is the difference in lightness, and $\Delta a^*$ and $\Delta b^*$ are the differences in the color space coordinates, a* and b*. In certain configurations, color value measurements can be made using a chromameter, with data collection in the L*a*b* color coordinate mode using standard procedures.

The film of the present invention, in various embodiments, disintegrates during use of the composition. In other embodiments, the film does not disintegrate during use of the composition. In some embodiments, the film releases a material, such as a functional material, into the carrier. As referred to herein. "disintegrate" refers to physical disruption of the film or fragment material, so as to produce a film or film fragments of reduced size compared to the original film. Such disruption may be through mechanical, chemical, or physical-chemical means. The disintegration can result, for example, from shearing, grinding, or exposure to elevated temperatures during use. In various dentifrice embodiments of the present invention, such disintegration results from brushing of the composition on the teeth of the subject using the composition. In one embodiment, the film disintegrates so as to release a functional material (as further described herein). In some embodiments, a film fragment can disintegrate into small pieces that are not visually discernable. In some embodiments, the film fragments disintegrate to collectively form a colloid or gel.

In various embodiments, the composition of the present invention passes a disintegration test. In a preferable Disintegration Test, one gram of a composition comprising a sample of film fragments is placed on top of a 2 inch (50.8 mm) magnetic star bar. The stir bar is placed into a transparent vessel, such as a 500 ml beaker containing 300 ml of water at 30° C. The water comprising the stir bar is then stirred for 5 minutes at 750 rpm. The water is then analyzed for the presence of broken and unbroken film fragments. The analysis can comprise straining the water through a mesh that is less than half an original long dimension of the film shape. This test will show if any pieces did not break up.

In one embodiment, the film of the present invention has a Dissolution Value operable to effect release of said functional material during use of said composition. As referred to herein, the Dissolution Value is measured in a test where a one-inch round circle of film is placed in a container of water, without stirring, at about 30° C. The Dissolution Value is then determined as the time lapsed until the film has disintegrated so that no piece of the film remains having a size greater than 0.25 (0.63 cm) inches in any dimension. In certain dentifrice embodiments, a plurality of fragments, disintegrate or dissolve under conditions of normal use within about two minutes. In various embodiments, the Disintegration Value is from about 2 seconds to about 200 seconds, from about 5 seconds to about 120 seconds, or from about 50 seconds to about 100 seconds. In some embodiments, the film comprises materials selected from the group consisting of water insoluble polymers, non-polymer film forming materials, and mixtures thereof to form stable film fragments, i.e., film fragments that do not disintegrate under normal intended use. In various embodiments, the films comprise a plurality of first film fragments having a first Disintegration Value, and a second plurality of second film fragments having a Disintegration Value that is significantly different than said first Disintegration Value.

The film of the present invention optionally comprises materials that affect the physical or functional characteristics of the film. Such additional substances can be, for example, emulsifiers, plasticizers, fillers, or texture modifiers. Fillers among those useful herein include inert starch particles and cellulose. Texture modifiers include cold water swellable, physically modified and pregelatenized starches, to increase the stiffness of polymeric films, such as those comprising hydroxyalkyl methyl cellulose. In the preparation of such starch products, the granular starch is preferably cooked in the presence of water and, optionally, an organic solvent at a temperature not higher than 10° C. higher than the gelatinization temperature. The obtained starch is then dried.

Pregelatinized corn starch useful herein is available commercially. A preferred starch is available under the trade designation Cerestar Polar Tex-Instant 12640 from the Cerestar Company. This Cerestar starch is a pregelatinized, stabilized and crosslinked waxy maize starch. It is readily dispersible and swellable in cold water. In its dry form, it is a white free flowing powder with an average flake size no greater than 180 micrometers and 85% of the flakes are smaller than 75 micrometers. It has a bulk density of 44 lbs/ft$^3$. The Cerestar starch has excellent cold storage and freeze-thaw stability. It has a rapid hydration rate and can reach extremely high viscosity without cooking. It has a smooth and creamy texture similar to cook-up starches. It also has excellent paste clarity and a bland flavor. In one embodiment, the pregelatinized starch is present in the film matrix in an amount ranging from about 5 to about 50% by weight and preferably about 10 to about 35% by weight. The hydroxyalkyl cellulose to starch ratio (by weight) may vary from about 1:3 to about 5:1 and preferably about 1:1 to about 4:1.

In one embodiment, the film comprises more than one layer. For example, a film can comprise a first layer comprising a polymer, one or more additional layers that provide a coating. The coating can be, for example, a shellac coating. A coating can comprise a layer on either or both sides of a polymer layer. Thus, in some embodiments, a process for making a multi-layered film can comprise forming a first layer of a film, such as a polymer layer, then coating the first layer with a second or subsequent layer of a coating material, for example shellac.

Functional Material:

In various embodiments, the films of the present invention comprise a functional material. As referred to herein, a "functional material" is a material having a desired utility in the oral or personal care composition. In various embodiments, such utilities are therapeutic, cosmetic, aesthetic, decorative, sensory or combinations thereof. In some embodiments, film flakes comprised by a composition can comprise a plurality of functional materials. Such functional materials can be incorporated within the film or comprise a coating on the surface of the film. In one embodiment, the compositions of the present invention comprise a plurality of first film fragments having a first functional material, and a plurality of second film fragments having a second functional material, wherein the second functional material differs from the first functional material.

In various embodiments, the functional material is a flavorant. In certain oral care embodiments, a flavorant is rapidly released as the fragments disintegrate during use of the product, delivering a breath freshening flavor or desired mouthfeel or sweetness into the oral cavity. Flavorants among those useful herein include synthetic flavor oils or a flavoring aromatics, oleo resins and extracts derived from plants, leaves, flowers, fruits and so forth, and combinations thereof. Representative flavor oils include spearmint oil, cinnamon oil, peppermint oil, clove oil, bay oil, thyme oil, cedar leaf oil, oil of nutmeg, oil of sage, and oil of bitter almonds. Flavorants can be used individually or in admixture. Commonly used flavors include mints such as peppermint, artificial vanilla, cinnamon derivatives, and various fruit flavors. In certain embodiments, the film comprises flavoring or food additive, such as those described in Chemicals Used in Food Processing, publication 1274 by the National Academy of Sciences, pages 63-258. In various embodiments, the film comprise a flavorant at a level of from about 1% to about 30% by weight of the film, or from about 8% to about 25% by weight of the film.

In some embodiments, the film also comprises a sweetener. Sweeteners among those useful herein include natural and synthetic sweeteners. In one embodiment, the sweetener is a water soluble sweetening agent such as a monosaccharide, a disaccharide or a polysaccharide. For example, water soluble sweetening agents include xylose, ribose, glucose (dextrose), mannose, glatose, fructose (levulose), sucrose (sugar), maltose, a soluble saccharin salt, i.e., a sodium or a calcium saccharin salt, a cyclamate salt, dipeptide based sweeteners, such an L-aspartic acid derived sweetener such as L-aspartyl-L-phenylalanine methyl ester (aspartame). In various embodiments, the film comprises a sweetener at a level of from about 0.01% to about 10% by weight of the film.

In various embodiments, the film comprises a therapeutic active. As referred to herein, a therapeutic active is a material that is useful for the prevention or treatment of a physiological disorder or condition. Such disorders or conditions include those of the oral cavity (including the teeth and gingiva), skin, hair, and eyes. The specific therapeutic active is preferably determined according to the desired utility of the composition. Such actives include the following.

A. antimicrobial agents, such as triclosan, cetyl pyridium chloride, domiphen bromide, quaternary ammonium salts, zinc compounds, sanguinarine, fluorides, alexidine, octonidine, EDTA, essential oils such as thymol, methyl salicylate, eucalyptol and menthol, and the like.

B. non-steroidal anti-inflammatory drugs, such as aspirin, acetaminophen, ibuprofen, ketoprofen, diflunisal, fenoprofen calcium, naproxen, tolmetin sodium, indomethacin, and the like, C. anti-tussives, such as benzonatate, caramiphen edisylate, menthol, dextromethorphan hydrobromide, chlophedianol hydrochloride, and the like, D. decongestants, such as pseudoephedrine hydrochloride, phenylepherine, phenylpropanolamine, pseudoephedrine sulfate, and the like, E. anti-histamines, such as brompheniramine maleate, chlorpheniramine maleate, carbinoxamme maleate, clemastine fumarate, dexchlorpheniramine maleate, diphenhydramine hydrochloride, diphenylpyraline hydrochloride, azatadine meleate, diphenhydramine citrate, doxylamine succinate, promethazine hydrochloride, pyrilamine maleate, tripelennamine citrate, triprolidine hydrochloride, acrivastine, loratadine, brompheniramine, dexbrompheniramine, and the like, F. expectorants, such as guaifenesin, ipecac, potassium iodide, terpin hydrate, and the like, G. anti-diarrheas, such a loperamide, and the like, H. $H_2$-antagonists, such as famotidine, ranitidine, and the like; and I. proton pump inhibitors, such as omeprazole, lansoprazole, and the like, J. general nonselective CNS depressants, such as aliphatic alcohols, barbiturates and the like, K. general nonselective CNS stimulants such as caffeine, nicotine, strychnine, picrotoxin, pentylenetetrazol and the like, L. drugs that selectively modify CNS function such as phenyhydantoin, phenobarbital, primidone, carbamazepine, ethosuximide, methsuximide, phensuximide, trimethadione, diazepam, benzodiazepines, phenacemide, pheneturide, acetazolamide, sulthiame, bromide, and the like, M. antiparkinsonism drugs such as levodopa, amantadine and the like.

N. narcotic-analgesics such as morphine, heroin, hydromorphone, metopon, oxymorphone, levorphanol, codeine, hydrocodone, xycodone, nalorphine, naloxone, naltrexone and the like, O. analgesic-antipyretics such as salycilates, phenylbutazone, indomethacin, phenacetin and the like.

P. psychopharmacological drugs such as chlorpromazine, methotrimeprazine, haloperidol, clozapine, reserpine, imipramine, tranylcypromine, phenelzine, lithium and the like. The amount of medicament that can be used in the films, can be dependent upon the dose needed to provide an effective amount of the medicament. Examples of doses for specific medicaments that can be delivered in a film comprised by a composition are reviewed in Example 23.

In various embodiments, such utilities are therapeutic, cosmetic, aesthetic, decorative, sensory, or combinations thereof. In non-limiting examples, functional materials useful herein include flavorants, fragrances, essential oils, emulsifying agents, thickening agents, colorants, cooling agents, sweeteners, binding agents, surfactants, sulfur precipitating agents, plasticizing agents, pharmaceutical actives, salivary stimulants, stain prevention actives, antimicrobial agents, vitamins, herbs and herbal extracts, amino acids, enzymes or other proteins, abrasives, anti-caries agents, whitening agents, odor control agents, breath freshening agents, tartar control actives, plaque control agents, periodontal actives, antiperspirant actives, deodorant actives, conditioning agents, moisturizers, hair colorants, and combinations thereof.

In various embodiments, therapeutic agents useful herein include anticaries agents, tartar control agents, antiplaque agents, periodontal actives, breath freshening agents, malodour control agents, whitening agents, antibacterials, steroids, anti-inflammatory agents, vitamins, proteins, conditioning agents, moisturizers, antiperspirant actives, deodorant actives, anesthetics, and mixtures thereof.

In certain oral care embodiments, the film comprises an oral care active, which is useful for the prevention or treatment of an oral care disorder or condition. Oral care actives among those useful herein include abrasives, anti-caries agents, tartar control agents, antiplaque agents, periodontal actives, breath freshening agents, malodour control agents, tooth desensitizers, salivary stimulants, whitening agents, and combinations thereof. Active materials among those useful herein are described in U.S. Pat. No. 6,596,298, Leung et al.

Tartar control agents among those useful herein include dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$; long chain polyphosphates such as sodium hexametaphosphate; and cyclic phosphates such as sodium trimetaphosphate. In some configurations, a polyphosphate is a beta.-phase calcium pyrophosphate, such as disclosed in U.S. Pat. No. 6,241,974, White, Jr. In some embodiments, the film comprises an anticalculus agent at a level of about 15 to 20% by weight of the film.

Odor reducing agents useful herein include sulfur precipitating agents. Such sulfur-precipitating agents include metal salts, such as a copper salt or a zinc salt. Such salts include copper gluconate, zinc citrate and zinc gluconate. In various embodiments, the film comprises sulfur precipitating agents at a level of from about 0.01 to about 30% by weight of film, from about 2% to about 2.5% by weight of film, or about 10% to about 20% by weight of film.

In a certain embodiments, the functional material comprises a saliva stimulating agent (a "succulent"). Such agents include those disclosed in U.S. Pat. No. 4,820,506, Kleinberg et al. In some configurations, a saliva stimulating agent can include a food acid such as citric, lactic, malic, succinic, ascorbic, adipic, fumaric and tartaric acids. In various embodiments, the film comprises a saliva stimulating agent at a level of from about 0.01 to about 12% by weight of the film, from about 1% to about 10% by weight of the film, or from about 2.5% to about 6% by weight of the film. In some embodiments, a saliva stimulating agent can be used in the amelioration of dry mouth.

In certain oral care embodiments, the film comprises other active materials, such as antibacterial agents such as magnolia extract, triclosan, grapeseed extract, thymol, methyl salicylate, eucalyptol, menthol, hop acids, cetyl pyridinium chloride, (including CPC/Zn and CPC+ enzymes) and usnic acid; anti-inflammatory agents such a breath freshening agents (for example zinc gluconate, zinc citrate, zinc chlorite and alpha ionone); tooth desensitizers such as potassium nitrate, desensitizing polymers, and desensitizing minerals; anti-inflammatory agents such as magnolia extract, ursolic acid; aloe, and cranberry extract; vitamins such as pantheon, retinyl palmitate, folic acid, tocopherol acetate and Vitamin A; herbs or herbal extracts such as rosemary, oregano, chamomilla recutita, mentha piperita, salvia officinalis, orcommiphora and myrrha; proteins, such as milk proteins and enzymes such as peroxide-producing enzymes, amylase, plaque-disrupting agents such as papain, glucoamylase, glucose oxidase, and "next generation" enzymes; whitening agents such as hydrogen peroxide, urea peroxide and phosphate salts; medicinals, such as aspirin (acetyl salicylic acid), caffeine, and benzocaine; probiotics; abrasives such as silicas (including high cleaning silica); anti-caries agents such as stannous salts (e.g., stannous fluoride) or amino fluoride; a nitric oxide synthase inhibitor such as guanidinoethyldisulfide; calcium; antiattachment ingredients, such as polyumylphosphonic acid; preservatives such as Solbrol® (Bayer Chemicals AG); silicones; chlorophyll compounds, anti-leukoplakia agents such as beta-carotene; antioxidants such as Vitamin E; and combinations thereof. In some embodiments, the films comprise such active materials at a concentration of about 0.01 to about 30% by weight of film, from about 2% to about 25% by weight of the film, or from about 10% to about 20% by weight of film.

In certain skin care embodiments, the functional material comprises a material selected from the group consisting of surfactants, conditioning agents, moisturizers, enzymes and other proteins, vitamin, and mixtures thereof.

In certain hair care embodiments, the functional material comprises a material selected from the group consisting of surfactants, colorants, denaturants, film forming polymers, conditioners, moisturizers, enzymes and other proteins, vitamins, antidandruff agents, and mixtures thereof.

In certain antiperspirant or deodorant embodiments, the functional material comprises a material selected from the group consisting of fragrances, alcohols, anticholinergics, antiperspirant salts (such as aluminum and zirconium salts), moisturizers, and mixtures thereof.

In various embodiments, the film comprises a compatibility enhanced active. As referred to herein, a "compatibility enhanced active" is a functional material that has enhanced utility in a composition wherein the material is a component of a film, relative to the utility of the material in a composition wherein the material is a component of the carrier. Such enhanced utility may be due to any of a variety of factors, including enhanced delivery or reduced physical or chemical degradation of the material. In some embodiments, the compatibility enhanced material is incompatible with a component or components of the carrier. A component which is incompatible with a carrier can be, for example, a component which reacts chemically or forms a precipitate with a component of the carrier.

Compatibility enhanced actives among those useful herein include cationic antimicrobials, calcium salts, fluoride salts, enzymes and other proteins, and other ingredients incompatible with anionic components, and mixtures thereof. In one dentifrice embodiment, a compatibility enhanced active is a cationic antimicrobial, such an antimicrobial comprising a quaternary group. Examples of such antimicrobials include cetyl pyridinium chloride (CPC), chlorhexidine, and ethyllauroylarginine HCl. Such actives are generally incompatible with carriers comprising the surfactant sodium lauryl sulfate (SLS, a common component of dentifrices) or silicate abrasives. For example, in such a composition, the CPC and SLS typically form a complex upon mixing. The formation of the complex renders both compounds ineffective for their intended purposes in a dentifrice. However, incorporation of CPC in a film in a dentifrice composition of this invention comprising both film and a carrier which comprises SLS will maintain both substances in the dentifrice in an effective state. Other examples of compatibility enhanced actives useful in dentifrice compositions of this invention include the anti-caries agent sodium fluoride (NaF), which is a component of some dentifrices, can be incompatible with calcium, which is also comprised by some dentifrices, because calcium fluoride ($CaF_2$), can form a precipitate. However, if one of these components (for example, sodium fluoride) is comprised by film fragments in an oral care composition, the composition can provide effective amounts of both calcium and the anti-caries agent.

In certain embodiments, the film comprises a preservative. A preservative can be added in amounts from about 0.001 wt % to about 5 wt %, preferably from about 0.01 wt % to about 1 wt % of the film. Non-limiting examples of preservatives include sodium benzoate and potassium sorbate.

In various embodiments, the present invention provides a dentifrice having entrained therein flakes of a water hydratable film comprised of a homogeneous mixture of a water soluble hydroxyalkyl cellulose polymer and, optionally, starch, the film matrix having entrained therein an agent selected from therapeutic, cosmetic, sensory, and decorative agents. In one embodiment there is provided an aesthetically decorative dentifrice having distributed throughout film flakes in which a decorative colorant is entrained in the film matrix, the dentifrice vehicle being substantially clear so that the aesthetically decorative effect can be viewed by the user. In various embodiments, therapeutic agents such as antibacterial agents and fluoride anticaries salts, are entrained in the film flake matrix. In various embodiments, sensory agents such as breath freshening agents, mouthfeel agents, and sweetening agents are entrained in the film flake matrix. In one such embodiment, the flavorants are rapidly released as the flakes disintegrate during toothbrushing, delivering a pleasing burst of sweetness or breath freshening flavor into the oral cavity.

In certain embodiments, the entrainment of the therapeutic, cosmetic, sensory and decorative agents in the film matrix suspended in the dentifrice or other composition isolates these agents from interaction with reactive ingredients present in the composition so that the agents are maintained substantially separate from the reactive composition ingredients during manufacture and storage while subsequently being released from the film matrix when the composition is used.

The films of the present invention may be made in a variety of ways, including methods among those known in the art for making films. In various embodiments, components of a film forming slurry, such as those disclosed in the Examples below, are mixed to form a film forming slurry composition. The slurry is cast on a releasable substrate and dried to form a sheet of film material. In one embodiment, the substrate material has a surface tension that allows the film slurry to spread substantially uniformly across the substrate surface, thereby avoiding formation of a destructive bond between the film and the substrate. Non-limiting examples of suitable substrates include glass, stainless steel, Teflon™ and polyethylene- or silicone-impregnated paper. Following casting, the film is then dried. Drying of the slurry can be carried out at high temperature with the aid of a drying oven, a drying terminal, a vacuum drier, or any other suitable drying equipment known in the art. In other embodiments, the film is made by extrusion of the film composition through a die, followed by cutting to a desired thickness, and drying. In other embodiments, the film is made by solvent casting.

In some embodiments, film fragments comprising a repeating shape, such as, for example, a geometric or representational shape, are formed from a slurry or a dried film. In certain configurations, forming of a shape can be by any method known to skilled artisans, such as, for example, adding a slurry to a substrate comprising a mold. In certain embodiments, a dried film can be cut or punched into a shaped film fragment.

The film fragments are incorporated in the base dentifrice of the present invention at a broad range of concentrations. In various dentifrice embodiments, the carrier comprises fragments at a level of from about 0.005% to about 5% by weight of the composition, or from about 0.05 to about 0.5% by weight of the composition.

Carrier:

The compositions of the present invention comprise a carrier in which a film, or fragments, is entrained. As referred to herein, a "carrier" is any material or composition in which a film can be entrained and is suitable for administration or application to the human or animal subject to whom the composition is administered or applied. As referred to herein, "entrained" refers to the embedding or suspension of a film in a carrier. In various embodiments comprising a plurality of fragments, such fragments may be entrained by embedding, suspension, dispersion or other distribution of the fragments in the carrier. In various embodiments, the fragments are distributed substantially homogenously throughout the carrier. In other embodiments, the fragments are not distributed homogenously in the carrier. In certain embodiments, the distribution of a plurality of film fragments is substantially isotropic within the carrier.

The compositions of the present invention may be described as comprising two phases, wherein one phase comprises a carrier and a second phase comprises a film or fragment. By "phase" as used herein is meant a physical phase as understood in the physical and material sciences, i.e., a portion of a material whose properties and composition are uniform. However, a phase as used herein can be discontinuous, i.e., a phase can comprise a plurality of separate components. For example, a plurality of polymer film fragments of identical composition is considered to comprise a single phase. In some embodiments, a film fragment can be entirely embedded within the material comprising the first phase, or totally or partially exposed on the surface of the first phase. For example, if the composition is a dentifrice comprising both a gel and film fragments, a film fragment can be totally surrounded by the gel, or partially or totally exposed on the surface of the gel. In certain embodiments, compositions comprise more than two phases. Such multi-phase compositions include those having two carriers, each of which contributes a phase to the composition, in addition to film fragments as described herein. Other multi-phase compositions include those having a single carrier and two or more pluralities of fragments, wherein the pluralities of fragments have differing compositions.

In certain embodiments, a composition comprising at least two phases can comprise one or more components which, while not necessary for the structure or stability of a composition, provide a beneficial or aesthetic effect. In some configurations, a component providing a beneficial or aesthetic effect can be a component which is incompatible with at least one phase of the composition. Such a component can be included in a different phase of the composition.

In various embodiments, the carrier is a liquid, semi-solid or solid. A "liquid" can be a liquid of low or high viscosity. A liquid can be a liquid of so that flow is imperceptible under ambient conditions. For example, a soap, such as an ordinary bar of hand soap, can be considered a liquid herein. A liquid can be a thixotropic liquid. A "semi-solid" as used herein can be a gel, a colloid, or a gum. As used herein, semi-solids and liquids are fluids distinguished on the basis of viscosity; a semi-solid is a high viscosity fluid, while a liquid has lower viscosity. There is no definitive dividing line between these two types of fluids. A semi-solid can, in certain embodiments, have a viscosity as high as thousands of mPa·s. Carriers among those useful herein include liquids, pastes, ointments, and gels, and can be transparent, translucent or opaque.

In certain embodiments, the compositions of the present invention are oral care compositions, suitable for administration to the oral cavity. Such compositions include dentifrices, mouthwashes, dental gels, lozenges, beads, gums, oral strips, mints, liquid toothpastes, sprays, paint-on gels, lip balms, whitening strips, breath strips, oral chews, and combinations thereof. An oral care composition disclosed herein can be used, for example, for cavity prevention, whitening, plaque prevention or reduction, gingivitis prevention or reduction, tartar control, sensitivity prevention or reduction, or breath malodor prevention or reduction, and stain prevention.

In certain embodiments, a composition comprising at least two phases can be a skin care composition, for example, a soap, a lotion, a body wash, a bath gel, a shampoo, a conditioner, a deodorant, an antiperspirant, a fragrance, a perfume, a cosmetic or combinations thereof, such as a antiperspirant/deodorant (ABDO). In certain embodiments, a composition comprising at least two phases can be a hair care composition, such as, for example, a shampoo or a conditioner, or a combination thereof.

The specific composition of the carrier preferably depends on the intended use of the composition. In various embodiments, the carrier is aqueous comprising from about 5% to about 95% water. In other embodiments, the carrier is substantially non-aqueous. In a dentifrice carrier, water content can be from about 5% to about 70%, from about 10% to about 50%, or from about 20% to about 40%.

The carrier may comprise any of a variety of materials, including emulsifiers, thickeners, fillers, and preservatives. In some embodiments, the carrier comprises a functional material, such as those described above. In some embodiments, the carrier comprises the same functional material as the film.

In one embodiment, the carrier is suitable for use as a dentifrice. In some embodiments, the carrier comprises a humectant, such as glycerine, sorbitol or an alkylene glycol such as polyethylene glycol or propylene glycol. In some configurations, the carrier comprises a humectant at a level of from about 10% to about 80% by weight, or about 20% to about 60% by weight of the composition. Carrier compositions among those useful herein are disclosed in U.S. Pat. No. 5,695,746, Garlick, Jr., et al., and U.S. Pat. No. 4,839,157, Mei-King Ng et al.

In various dentifrice embodiments, the carrier comprises thickeners, gelling agents or combinations thereof. Thickeners or gelling agents useful herein include inorganic, natural or synthetic thickeners or gelling agents. In some configurations, the carrier comprises the thickener and gelling agent at total levels of from about 0.10% to about 15% by weight, or from about 0.4% to about 10% by weight of the composition. Examples of thickeners and gelling agents useful herein include inorganic thickening silicas such as: an amorphous silica, for example Zeodent® 165 (Huber Corporation); Irish moss; iota-carrageenan; gum tragacanth; or polyvinylpyrrolidone. In certain embodiments, the carrier comprises a polishing agent, such as a silica, a calcined alumina, sodium bicarbonate, calcium carbonate, dicalcium phosphate or calcium pyrophosphate. In various embodiments, the carrier can be a visually clear composition.

In various dentifrice embodiments, comprising a visually clear carrier, the composition comprises at least one polishing agent. Polishing agents among those useful herein include collodial silica, such as, for example, Zeodent® 115 (Huber Corporation), and alkali metal aluminosilicate complexes (i.e., a silica comprising alumina). In some configurations, a polishing agent can have a refractive index close to that of a gelling agent combined with water and/or humectant. In various embodiments, the carrier comprises the polishing agent at a level of from about 5% to about 70% by weight of the composition.

In certain dentifrices, the carrier comprises a surfactant or mixture of surfactants. Surfactants among those useful herein include water-soluble salts of at least one higher fatty acid monoglyceride monosulfate, such as the sodium salt of the monsulfated monoglyceride of hydrogenated coconut oil fatty acids; cocamidopropyl betaine; a higher alkyl sulfate such as sodium lauryl sulfate; an alkyl aryl sulfonate such as sodium dodecyl benzene sulfonate; a higher alkyl sulfoacetate; sodium lauryl sulfoacetate; a higher fatty acid ester of 1,2-dihydroxy propane sulfonate; and a substantially saturated higher aliphatic acyl amides of a lower aliphatic amino carboxylic acid, such as those having 12 to 16 carbons in the fatty acid, alkyl or acyl radicals; and mixtures thereof. Amides can be, for example, N-lauroyl sarcosine, and the sodium, potassium, and ethanolamine salts of N-lauroyl, N-myristoyl, or N-palmitoyl sarcosine. In various embodiments the carrier comprises the surfactant at a level of from about 0.3% to about 5% by weight of composition, or about 0.5% to about 3% by weight of composition.

The present invention also provides methods for making a dentifrice carrier. In one embodiment, water and at least one humectant are dispersed in a conventional mixer until a first homogeneous gel phase is formed. A polishing agent is added into the first homogeneous gel phase. The first homogeneous gel phase and the polishing agent are mixed until a second homogeneous gel phase is formed. A thickener, flavorant and surfactants are added to the second homogeneous gel phase. These ingredients are mixed at high speed tinder vacuum of about 20 to 100 mmHg.

In some embodiments, a composition comprising a carrier and a plurality of film fragments can be suitable for use as a body cleansing formulation, such as, for example, a soap, or a soap-based gel formulation. In these embodiments, a carrier can comprise a cleansing formulation such as, in non-limiting example, a polyethylene glycol diisostearate such as disclosed in U.S. Pat. No. 6,531,119, Hall-Puzzio, et al. In certain embodiments, a composition comprising a carrier and a plurality of film fragments, wherein the carrier comprises a cleansing formulation can comprise a polyethylene glycol diisostearate having an average degree of ethoxylation of from 40-100. The diisostearate can be, in certain configurations, a component of a soap-based gel composition. In some embodiments, the diisostearate can be suitable for use in stable cosmetic compositions, especially as antiperspirants and/or deodorants, and which diisostearate is compatible with such formulations.

In some embodiments, a composition comprising a carrier and a plurality of film fragments can be suitable for use as a cosmetic, such as, for example, a mascara formulation that is removable with soap and water. In these embodiments, the carrier can be a mascara formulation such as disclosed in U.S. Pat. No. 6,503,495, Alwattari et al. In certain configurations, these carrier compositions can comprise from about 3% to about 60% water-insoluble polymeric material, from about 2% to about 50% water-soluble, film-forming polymers, and from about 0.05% to about 20.0% organophilic clays. In certain embodiments, these compositions can be fabricated in a multitude of forms, such as creams, pastes and solids. In some embodiments, a mascara carrier composition can comprise a water-insoluble polymeric materials in an aqueous emulsion. In certain embodiments, water-insoluble polymeric materials, can be aqueous emulsions or dispersions of polymeric materials comprising polymers. In some configurations, the polymers can comprise precursor monomers, mixtures of monomers, natural polymers and mixtures thereof. In some configurations, a polymeric material can also include water-insoluble polymeric materials. In certain configurations, a water-insoluble polymer can comprise from about 3% to about 60%; from about 4% to about 40%, or from about 5% to about 30% by weight of the composition. In non-limiting example, a water-insoluble polymeric material can comprise monomers selected from the group consisting of aromatic vinyls, dienes, vinyl cyanides, vinyl halides, vinylidene halides, vinyl esters, olefins and their isomers, vinyl pyrrolidone, unsaturated carboxylic acids, alkyl esters of unsaturated carboxylic acids, hydroxy derivatives of alkyl esters of unsaturated carboxylic acids, amides of unsaturated carboxylic acids, amine derivatives of unsaturated carboxylic acids, glycidyl derivatives of alkyl esters of unsaturated carboxylic acids, olefinic diamines and isomers, aromatic diamines, terephthaloyl halides, olefinic polyols and mixtures thereof.

In some embodiments, a composition comprising a carrier and a plurality of film fragments can be suitable for use as an antiperspirant, a deodorant, or an antiperspirant-deodorant (ABDO), such as, for example, an antiperspirant. A carrier of these embodiments can comprise an antiperspirant composition such as, for example, an antiperspirant composition disclosed in U.S. Pat. No. 6,524,562, Guskey. In these embodiments, a carrier can be, for example, a single-phase system comprising a solubilized antiperspirant active, a silicone elastomer and a volatile silicone. In some embodiments, a antiperpirant carrier can also comprise a structurant.

In some embodiments, a composition comprising a carrier and a plurality of film fragments can be suitable for use as a shampoo, such as, for example, an antidandruff shampoo. A carrier of these embodiments can comprise an antidandruff composition such as, for example, an antidandruff composition disclosed in U.S. Pat. No. 4,470,982, Winkler. In certain embodiments, a carrier can be, for example, an antidandruff shampoo composition comprising anionic surfactant, a suspending agent and an alkanol amide. In some embodiments, a surfactant can be an alkyl sulfate, an ethoxylated alkyl sulfate or mixtures thereof. In some configurations, an alkyl sulfate can be the sodium, ammonium and triethanolamine alkyl sulfates having from about 8 to about 22 carbon atoms in the alkyl chain, or from about 8 to about 18 carbon atoms in the alkyl chain, or from about 8 to about 18 carbon atoms. In certain embodiments, a suspending agent can comprise, in non-limiting example, ethylene glycol esters of fatty acids having from about 16 to about 22 carbon atoms, such as, for example, ethylene glycol stearates, both mono and distearate, or alkanol amides of fatty acids, having from about 16 to about 22 carbon atoms, or about 16 to 18 carbon atoms. An alkanol amide can be a stearic monoethanolamide, stearic diethanolamide, stearic monoisopropanolamide and stearic monoethanolamide stearate. In certain embodiments, an amide can be any alkanolamides of fatty acids known for use in shampoos. In certain configurations, these can be generally mono- and diethanolamides of fatty acids having from about 8 to about 14 carbon atoms, such as coconut monoethanolamide, lauric diethanolamide and mixtures thereof. In certain embodiments, an antidandruff carrier can comprise a particulate antidandruff agent. In some configurations, these can be, for example, sulfur, selenium sulfide, salicylic acid, zinc pyridinethione, other 1-hydroxy pyridones, such as those disclosed in U.S. Pat. No. 4,185,106, Dittmar et al. and azole antimycotics disclosed in British Pat. No. 1,502,144, Feb. 22, 1978.

In some embodiments, a composition comprising a carrier and a plurality of film fragments can be suitable for use as a lotion, such as, for example, lotion disclosed in U.S. Pat.

No. 6,352,701 to Scholz et al., which is hereby incorporated by reference in its entirety. In some configurations, a lotion carrier can have a very nice feel after both single and multiple applications. In some configurations, a composition comprising a lotion carrier and a plurality of film fragments can maintain or improve the skin condition after multiple applications without noticeable slimy or abnormal feeling during post application hand washing. In some aspects, when used as a presurgical scrub replacement, a composition comprising a lotion carrier and a plurality of film fragments can achieve bacterial, fungal, and viral kill equal to or better than a traditional soap and water scrub in a shorter period of time while maintaining or improving the skin's natural barrier to microbial and chemical contaminants. In certain embodiments, a composition comprising a lotion carrier and a plurality of film fragments can provide a viscous composition which includes a high concentration of a lower alcohol but does not require a polymeric thickener to make the composition viscous. Further, in certain aspects, a composition comprising a lotion carrier and a plurality of film fragments can have a cosmetically elegant feel and may be dispensed as a lotion or as a foam.

A composition comprising a lotion carrier and a plurality of film fragments can comprise a lower alcohol and water in a weight ratio of about 35:65 to 100:0, between at least 0.5% and 8.0% by weight thickener system comprised of at least two emulsifiers, each emulsifier present in at least 0.05% by weight wherein the emulsifiers can be selected such that the composition free of auxiliary thickeners has a viscosity of at least 4,000 centipoise at 23 degrees C. and wherein each emulsifier can be comprised of at least one hydrophobic group and at least one hydrophilic group, wherein: (i) the hydrophobic group can be comprised of an alkyl group of at least 16 carbon atoms; an alkenyl group of at least 16 carbon atoms; or an aralkyl or an aralkenyl group of at least 20 carbon atoms; and (ii) the hydrophilic group of at least one emulsifier can be comprised of an amide group having the structure —NHC(O)R''' or —C(O)NHR''' where R''' can be hydrogen or an alkyl group of 1-10 carbon atoms optionally substituted in available positions by N; O, and S atoms; an ester group of short chain alcohols or acids (e.g., L=—C(O) OR' or —OC(O)R' where R' can be $C_1$-$C_4$ branched or straight chain alkyl optionally substituted in available positions by hydroxyl groups); a polyglucoside group having 1-10 glucose units; a polyglycerol ester group having 1-15 glycerol units, a secondary amine group; a tertiary amine group; a quaternary amine group; an anionic group such as a sulfate, a sulfonate group, a phosphate group, a phosphonate group, a carboxylate group, or a zwitterionic group.

In certain embodiments, the films and carriers of the present invention are comprised so as to maximize aesthetic acceptability of the composition. As referred to herein, "aesthetic acceptability" refers to the acceptability of the composition to the intended user of the composition according to one or more non-functional characteristics, such as appearance (including color and texture), flavor, scent, and mouthfeel. A film fragment or a composition comprising film fragments can be tested for aesthetic appeal through the use of hedonic testing, including the use of methods among known in the art. For example, a standard testing procedure for sensory evaluation can comprise providing samples to a panel of testers who rate the samples using a 9-point hedonic scale as described.

| Score/rating | Std. Hedonic Scale |
| --- | --- |
| 9 | like extremely |
| 8 | like very much |
| 7 | like moderately |
| 6 | like slightly |
| 5 | neither like nor dislike |
| 4 | dislike slightly |
| 3 | dislike moderately |
| 2 | dislike very much |
| 1 | dislike extremely |

A film or composition scoring above neutral on a 9-point hedonic scale. i.e. 5.0 or greater, for at least one, more preferably two and most preferably all sensory characteristics of shape, color, flavor, mouthfeel and texture can be considered to be acceptable with respect to the measured attributes. Thus, for example, a panel comprising at least ten testers provided with film fragments comprising a particular shape, or a multi-phase composition comprising film fragments of a particular shape (e.g., a dentifrice comprising square film fragments), can rate the film fragments or the composition for traits such as, for example shape, color, flavor, strength, foam, aftertaste, feel clean, impact, mouthfeel, texture and overall liking according to the above scale. In certain embodiments, the shape of film fragments affect a users response to traits such as color, flavor, strength, foam, aftertaste, feel clean, impact, mouthfeel, texture and overall liking. In certain embodiments, the nature of the product being tested, or the purpose of the product indicated to the testers, affect the hedonic response by a tester.

The compositions of the present invention are preferably stable under normal conditions of storage. As referred to herein, "stable" refers to the lack of significant adverse effect on one, and preferably all, compositional attributes such as appearance, flavor, rheology, and chemical composition of the composition. Preferably, stability in the present compositions includes the compositional and physical stability of film (including fragments, if any) in the composition. In various embodiments a composition comprising a film is stable upon storage at ambient temperature for at least about two years. It is understood, however, that in some embodiments, an otherwise stable film can disintegrate during use (as discussed above), for example, during toothbrushing using a dentifrice composition.

In certain embodiments, a composition can comprise, in addition to film fragments as described herein, two or more carriers, each of which contributes a phase to the composition. Such a composition can be stable to color bleeding. For example, a composition can include film fragments and a striped dentifrice such as that disclosed in U.S. Pat. No. 6,315,986, Wong et al. In certain embodiments, the film fragments can be of different color(s) than the stripe(s) for enhanced aesthetic appeal.

Manufacturing Processes:

The present invention provides processes for making compositions comprising a film entrained in a carrier. In various embodiments, a plurality of fragments are combined with a carrier. In some configurations, a carrier and a plurality of film fragments can be mixed. In some configurations, the mixing can comprise slow stirring. In one embodiment, the present invention provides a process for making a composition comprising a carrier having distributed therein a plurality of lamellar fragments, wherein said process comprises:

(a) providing said carrier;
(b) adding said lamellar fragments to said carrier to form a mixture; and
(c) homogenizing said mixture.

As referred to herein, "homogenizing" refers to the admixture of the fragments and the carrier so as to attain a substantially homogeneous distribution of fragments in the carrier. It should be noted, however, that the resulting composition still retains two-phase composition. Homogenizing may be accomplished using any of a variety of conventional homogenizers.

In another method, the film is added to a component of the carrier (e.g., to a humectant for a dentifrice). The rest of the carrier is then made, and the mixture of film is then added to the carrier.

Methods of Use:

The present invention provides methods for the administering a functional material to a human or animal subject. As referred to herein, "administering" refers to any method by which a composition is applied on or administered to the subject. In various embodiments, the administration is topical, wherein the composition is applied to an external surface of the subject, such as to a surface of the oral cavity (e.g. teeth, gingival, and tongue), to the skin, to the eye, and to the hair. The specific route and method of administration will depend, of course, on the intended use of the composition.

In various embodiments, the present invention provides methods for administering a functional material to a human or animal subject in need thereof, comprising topically applying to said subject a composition comprising a film entrained in a carrier, wherein said film comprises the functional material. In one embodiment, the method additionally comprises disrupting the film after topically applying the film. Such disruption may be accomplished by any of a variety of methods, including chemical and/or mechanical means. Chemical means include degradation of the film by contact with water or a material present at the site of administration (e.g., saliva in an oral care application). Physical means include agitation, grinding, and shear forces produced by application of physical energy to the composition during use (e.g., brushing in a dentifrice application).

In various embodiments, the present invention provides methods for the treatment of an oral care condition. As referred to herein, an "oral care condition" is any disorder or condition which can be prevented or treated by administration of a composition to the oral cavity, including disorders or conditions of the teeth, oral mucosa, gingiva and tongue. Such conditions include caries, gingivitis, periodontitis, and cosmetic conditions such as yellowing and malodour.

In one embodiment, the present invention provides a method for enhancing whole body health, by administering a composition of the present invention to the oral cavity. By "whole body health" as used herein is meant overall systemic health characterized by a reduction in risk of development of systemic diseases, such as major systemic diseases such as cardiovascular disease, stroke, diabetes, severe respiratory infection, premature and low birth weight infants (including associated post-partum dysfunction in neurologic/developmental function), and associated increased risk of mortality. In various such embodiments, one or more phases of a composition comprise a functional material. In various embodiments, the film comprises the functional material; in other embodiments, the carrier comprises the functional material; in other embodiments, both the carrier and the film comprise such functional materials. In one embodiment, the functional material is an oral care active. In one embodiment, the functional material can provide a health benefit that is non-exclusive to oral health, for example a functional material can contribute to the amelioration, risk reduction, treatment or prevention of disease, dysfunction, or other abnormality. Such materials among those useful herein include those described in PCT Publication WO 02/02128 A2, Doyle et al. The disease, dysfunction or abnormality can affect one or more body parts. A composition can promote whole body health by promoting oral health. For example, a composition can reduce the risk of the development of cardiovascular disease, stroke, atherosclerosis, diabetes, respiratory infection, premature birth, low birth weight, post-partum dysfunction in neurologic and developmental functions, and associated risk of mortality. For example, enhancement of whole body health by treatment of the oral cavity can be evidenced by the following health indicia:

1) reduction in risk of development of heart attack, stroke, diabetes, severe respiratory infections, low birth weight infants, and postpartum dysfunction in neurologic/developmental function and associated increased risk of mortality;
2) reduction in the development of fatty arterial streaks, atherosclerotic plaques, progression of plaque development, thinning of the fibrous cap on atherosclerotic plaques, rupture of atherosclerotic plaques, and the subsequent blood clotting events;
3) reduction in carotid arterial (intimal) wall thickness (e.g., as assessed by ultra-sound techniques);
4) reduction in exposure of blood and systemic circulation to oral pathogens and/or their toxic components, specifically leading to reduction in blood levels of oral bacteria, lipopolysaccharide (LPS) and/or the incidence of oral pathogens and/or components thereof found in arterial plaques, arterial structures, and/or distant organs (e.g. heart, liver, pancreas, kidney);
5) reduction in exposure of the lower respiratory track to the inhalation of bacterial pathogens and the subsequent development of pneumonias and/or exacerbation of chronic obstructive lung disease;
6) reduction in alterations in circulating hematocrit, hemoglobin, white blood cell count and/or platelet counts;
7) reduction in the incidence of disregulation in blood/serum levels of inflammatory mediators/cytokines such as TNF-alpha, IL-6, CD-14, and IL-1;
8) reduction in the incidence of disregulation of blood/serum levels of acute phase reactants including C-reactive protein, fibrinogen, and haptoglobin;
9) reduction in the incidence of disregulation of blood/serum markers of metabolic disregulation including homocysteine, glycosylated hemoglobin, 8-iso-PGF-2alpha, and uric acid;
10) reduction in incidence of disregulation of glucose metabolism as typically assessed by impaired glucose tolerance test, increased fasting blood glucose levels, and abnormal fasting insulin levels; and
11) reduction in disregulation of blood lipid levels specifically including blood or serum cholesterol, triglycerides, LDL, HDL, VLDL, Apolipoprotein B, and/or Apolipoprotein A-1.

The present invention can be further understood by reference to the following non-limiting examples.

EXAMPLE 1

This example illustrates, in table 1, a slurry formulation that can be used to make menthol-flavored white films.

TABLE 1

| Ingredients | % Composition of Slurry | % Composition (dry) |
|---|---|---|
| Water | 80.65% | 5.00% |
| Methylcellulose E15 | 3.90% | 19.15% |
| Methylcellulose E50 | 3.90% | 19.15% |
| Menthol | 4.40% | 21.60% |
| Canola Oil | 2.60% | 12.76% |
| Titanium dioxide | 2.00% | 9.82% |
| Solka - floc 300 | 1.60% | 7.86% |
| Tween 80 | 0.25% | 1.23% |
| Glycerin | 0.25% | 1.23% |
| Triacetin | 0.25% | 1.23% |
| Cornstarch | 0.20% | 0.98% |
| % Solids | 19.35% | |
| Total | | 100.00% |

EXAMPLE 2

This example illustrates slurry formulations comprising titanium dioxide (TiO$_2$). In this example, the formulation of either Example 1 or Example 2 can be modified by substituting mica coated titanium dioxide (such as Timiron®, Merck & Co., Inc.) for titanium dioxide.

EXAMPLE 3

This example illustrates, in Table 2, a formulation of a film slurry composition that can provide a silver film, and a method of making the film slurry.

TABLE 2

| Ingredients | % Composition Of Slurry |
|---|---|
| Methylcellulose E15* | 3.92% |
| Methylcellulose E50* | 3.92% |
| Cerestar cornstarch 12640 | 0.392% |
| Solka —floc 300 | 1.57% |
| Tween 80 | 0.474% |
| Canola Oil | 0.949% |
| Timeron | 2.00% |
| Water to make | 100% |

*Methylcellulose E15 and methylcellulose E50 are hydroxypropyl methylcellulose food grade polymers (Methocel ™; Dow Chemical Co.).

EXAMPLE 4

This example illustrates, in Table 3, a formulation of a film slurry composition that provides a blue film.

TABLE 3

| Ingredients | % Composition Of Slurry |
|---|---|
| Methylcellulose E15* | 3.92% |
| Methylcellulose E50* | 3.92% |
| Cerestar cornstarch 12640 | 0.392% |
| Solka —floc 300 | 1.57% |
| Tween 80 | 0.474% |
| Canola Oil | 0.949% |
| Blue Poly 100 | 1.00% |
| Timeron | 1.00% |
| Water to make | 100% |

*Methylcellulose E15 and methylcellulose E50 are hydroxypropyl methylcellulose food grade polymers (Methocel ™; Dow Chemical Co.).

EXAMPLE 5

This example illustrates, in Table 4, a dentifrice carrier in which film fragments, such as those of Example 1, are unstable. In this example, the instability can be manifested by a spreading and deforming of the shapes, to 10% greater than the original size, typically to about 50% greater than the original size. The spreading and deformation generally occur at room temperature within one week. Once the shapes are spread out and deformed, the shapes may be no longer clearly observed through the packaging or during use (e.g., on the brush in the case of a dentifrice). A multi-phase composition comprising these film fragments (such as a dentifrice) that is subjected to mild force, for example through squeezing a tube or shaking a bottle comprising the composition, disrupts these film fragments.

TABLE 4

| Ingredient | Wt % |
|---|---|
| Sodium CMC | 0.65 |
| Polyethylene glycol 600 (PEG-12) | 3.0 |
| Sorbitol (70% in water) | 57.69 |
| Sodium saccharin | 0.3 |
| Sodium fluoride | 0.24 |
| Tetrasodium pyrophosphate | 0.5 |
| FD&C Blue #1 dye (1.25% in water) | 0.4 |
| Silica abrasive (Sylodent XWA 650) | 20 |
| Silica thickener (Zeodent 165) | 4.25 |
| Flavor oil | 1.15 |
| Sodium lauryl sulfate (29% in water) | 5.172 |
| White, flavored films | 0.3 |
| Water | Q.S. |

EXAMPLE 6

Example illustrates, in Table 5, a dentitrice carrier in which film fragments are entrained and remain stable. In a composition comprising shaped film fragments of this formulation, the shapes can withstand squeezing, shaking, etc. without losing their distinct size and shape.

TABLE 5

| Ingredient | Wt % |
|---|---|
| Sodium CMC | 0.65 |
| Polyethylene glycol 600 (PEG-12) | 3.0 |
| Sorbitol | 57.69 |
| Sodium saccharin | 0.3 |
| Sodium fluoride | 0.24 |
| Tetrasodium pyrophosphate | 0.5 |
| FD&C Blue #1 dye (1.25% in water) | 0.4 |
| Silica abrasive (Sylodent XWA 650) | 20 |
| Silica thickener (Zeodent 165) | 4.25 |
| Flavor oil | 1.15 |
| Sodium lauryl sulfate (29% in water) | 5.172 |
| Cocamidopropyl betaine (35% in water) | 1.25 |
| White, flavored films | 0.3 |
| Water | Q.S. |

This example illustrates, in the following Table, a dentifrice formulation that can be used to form a stable dentifrice composite. In a composition comprising shaped film fragments of this formulation, the shapes can withstand squeezing, shaking, etc. without losing their distinct size and shape.

| Ingredients | Wt % |
| --- | --- |
| Xanthan Gum | 0.45 |
| Polyethylene glycol 600 OPEG-12) | 3.0 |
| Sorbitol | 66.638 |
| Sodium saccharin | 0.3 |
| Sodium fluoride | 0.24 |
| Tetrasodium pyrophosphate | 0.5 |
| FD&C Blue #1 dye (1.25% in Water) | 0.4 |
| Silica abrasive (Sylodent XWA 650) | 10.0 |
| Silica thickner (Zeodent 165) | 2.50 |
| Flavor Oil | 1.15 |
| Sodium lauryl sulfate (29% in water) | 5.172 |
| Cocamidopropyl betaine | 1.25 |
| White, flavored films | 0.2 |
| Water | Q.S. |

EXAMPLE 8

This examples illustrates, in Table 6, a slurry formulation that can be used to make a menthol-flavored white film.

TABLE 6

| Ingredients | % Composition of Slurry |
| --- | --- |
| Water | 72.5 |
| Methylcellulose E5 | 10 |
| Methylcellulose E50 | 3 |
| Menthol | 4.375 |
| Cornstarch | 4 |
| Canola Oil | 2.625 |
| Titanium Dioxide | 1 |
| Tween 80 | 0.5 |
| Propylene Glycol | 2 |
| % Solids | 27.5 |
| Total | 100.00 |

EXAMPLE 9

This example illustrates, in Table 7, a slurry formulation that can be used to make menthol-flavored green film.

TABLE 7

| Ingredients | % Composition of Slurry |
| --- | --- |
| Water | 73.95 |
| Methylcellulose E5 | 9.55 |
| Menthol | 6.875 |
| Cornstarch | 4 |
| Canola Oil | 4.125 |
| Pigment Green 7 (50%) | 1 |
| Tween 80 | 0.5 |
| TP-206 Carageenan | 0.10% |
| % Solids | |
| Total | 100.00 |

EXAMPLE 10

This example illustrates a procedure for making a film dentifrice composition, such as in Example 6. In this procedure, carboxymethylcellulose (CMC) is dispersed in polyethyleneglycol 600 (PEG 600). NaF and saccharine are dissolved in water in separate vessel. Sorbitol is mixed into the CMC/PEG portion, followed by a water/salts solution. Tetrasodium pyrophosphate (TSPP) is added, then a blue dye such as FD&C Blue #1. Silicas are then added, and mixed under vacuum. Betaine. SLS and flavor are added and mixed under vacuum, followed finally by white flavored films.

EXAMPLE 11

This example illustrates a procedure for making a composition disclosed herein, such as in Example 6.

Part I—Formula Ingredients: Purified Water, Sodium Fluoride

Weigh or meter purified water to the slurry tank. With the agitator on add formula amount of sodium fluoride. Mix for 10 minutes minimum.

Part II—Formula Ingredients: PEG, CMC, TSPP, Saccharin

Weigh or meter PEG to dispersion tank. Add formula amount of CMC, TSPP and saccharin. Mix for 15 minutes minimum.

Part III—Formula Ingredients: Sorbitol, Part II, Part I

Weigh or meter formula amount of sorbitol to the main mixer. Increase vacuum and start agitation. Transfer PART II to the mixer. Transfer the mixture from PART I to the mixer. Mix for 15 minutes minimum under full vacuum.

Part IV—Formula Ingredients: Color Solution, Zeodent 165, XWA 650, Flavor

Stop agitation and release vacuum. Add color solution. Increase vacuum and start agitation. With the mixer at high speed (and homogenizer on) add formula amounts of ZEODENT 165, and XWA 650. During the addition of the powders add flavor (if Temperature<110 F). Increase vacuum until 28" minimum is reached. Mix under full vacuum for 15 minutes.

Part V—Formula Ingredients: Liquid SLS, Betaine, Film Fragments

Add formula amount of BETAINE with no vacuum and mixer speed at 25%. Apply full vacuum. Add formula amount of LIQUID SLS under full vacuum, 50% mixing speed and NO Homogenizer. Increase mixing speed to 100% and mix for 10 minutes minimum under full vacuum. Stop mixer and release vacuum. Add film fragments to mixer. Start agitation at 25% and mix for two minutes. Increase vacuum to 28" minimum. Increase agitation to 100% and mix for 10 minutes minimum. Stop mixer and release vacuum. Inspect the product and take sample. Pump batch through homogenizer (pump speed 100%, homogenizer speed 50%) to tote or portable storage tank.

EXAMPLE 12

This example illustrates determination of color contrast by determination of color space coordinates. Color space coordinates of the film and the toothpaste separately can be determined separately. As discussed supra, L a*b* values represent color values in a color space defined by the system established by the Commission Internatioanle d'Eclairage (CIE). Table 8 below shows the L a*b* values for a white film such and a corresponding blue toothpaste. This analysis reveals large differences in both the lightness, L*, as well as in the color parameters, a* and b*. As would be expected for a white film, a* and b* are close to 0 for the film.

TABLE 8

L*a*b* Color and Color Difference, ΔE*

| Sample | L* | a* | b* | ΔE*[a] |
|---|---|---|---|---|
| White film with menthol | 89.74 | −0.49 | 1.97 | — |
| Blue whitening toothpaste | 36.82 | 19.10 | 42.47 | 69.46 |

[a]Color difference, ΔE*, is relative to the white film.

To perform these measurements a Minolta CR-321 chromameter is used, with data collection in the L*a*b* color coordinate mode. The samples are each placed on a matching white background. One layer of film or 1" of toothpaste is placed on the detector and sandwiched on top by the white background.

EXAMPLE 13

This example illustrates silver colored, star shaped film fragments and a method for their production. Components of a film forming slurry used to make the film fragments are listed in Table 9 below. In preparing the film, the HMPC polymer Methocel E5LV having a viscosity of 5.1 mPa·s (2% aqueous solution) are added to deionized water at 23° C., and the solution stirred for 5 minutes. To this solution is added the pregelatized starch Cerestar Polar Tex Instant 12640. The combined ingredients are stirred vigorously for about one hour until the starch is completely dispersed and a homogeneous mixture is formed. To this mixture is added the titanium coated mica. The combination is mixed for 10 minutes, after which the sodium lauryl sulfate surfactant is added and mixed in for an additional 15 minutes. Thereafter spearmint flavor is added, and the slurry is thoroughly mixed for an additional 40 minutes to form a slurry emulsion. The weight ratio of HPMC to Starch is 2:1. The emulsion is then cast on a polyethylene coated paper at 25° C. and dried at 110° C. to form a solid thin film having a thickness of 2.5 microns. The film is then punched with a star-shaped punch. Resulting star shaped film fragments are each 0.25 inch (6.35 mm) in their longest dimension.

TABLE 9

Silver Film Matrix

| Ingredients | Wt. % |
|---|---|
| Starch | 21.0 |
| HPMC | 40.0 |
| Glycerin | 5.0 |
| Vegetable oil | 3.0 |
| Tween 80 | 1.0 |
| SLS | 1.0 |
| Sodium saccharin | 0.3 |
| Titanium coated mica | 3.8 |
| Flavor | 24.6 |
| Zinc gluconate | 0.3 |
| Total | 100 |

EXAMPLE 14

This example illustrates a composition and method for the production of a transparent green dentifrice carrier material. A transparent green colored base dentifrice composition having the ingredients listed in Table 9 is prepared, wherein a vehicle solution comprising the sorbitol and water is made and subjected to 28-30 inches Hg applied vacuum. A mixture of saccharin sodium fluoride and is added thereto. Subsequently, a green dye is blended with the vehicle. The mixture is degassed at 28-30 inches Hg applied vacuum over a 5 minute period. Then Zeodent 115 silica abrasive and Zeodent 165, an amorphous silica thickening agent and sodium lauryl sulfate (SLS) are added after preliminary degassing. The ingredients are mixed. After about 5 minutes mixing, with application of vacuum, the dentifrice preparation is considered to be complete.

TABLE 10

Green Base Dentifrice

| Ingredients | Wt. % |
|---|---|
| PEG 600 | 3.0 |
| Sodium carboxymethyl cellulose | 0.55 |
| Sorbitol | 74.0 |
| Purified water | 6.357 |
| Sodium fluoride | 0.243 |
| Tetrasodium pyrophosphate | 0.50 |
| Sodium saccharine | 0.30 |
| Zeodent 115 | 4.0 |
| Zeodent 165 | 8.8 |
| Sodium lauryl sulfate | 1.2 |
| Flavor | 1.0 |
| FD&C Green (2% soln.) | 0.05 |
| Total | 100 |

EXAMPLE 15

This example illustrates a method of producing a composition comprising a green dentifrice base carrier formulation and star shaped film fragments. To make the composition, star shaped film fragments of Example 13 are combined with transparent green dentifrice carrier material of Example 14, in a 0.3% (weight/weight) film:carrier ratio. The composition is thereafter packaged in a standard toothpaste tube.

After packaging, a sample of the dentifrice composition is squeezed from a tube and extruded as a distinctive green, aesthetically pleasing ribbon composition having suspended therein clearly visible star shaped silver colored film fragments extending throughout the extruded composition.

EXAMPLE 16

This example illustrates red, heart shaped film fragments and a method for their preparation. Red, heart shaped film fragments were prepared using a film prepared according to the procedure of Example 13 using dried film comprising the ingredients listed in Table 11 below. After drying of the film, shellac (100% non-bleached) is applied to the film. The final thickness of the film was 3.0 microns. Heart shaped film fragments, each 0.125 inch (3.28 mm) in their longest dimension, are then die cut from the film.

TABLE 11

Red Film

| Ingredients | Wt. % |
|---|---|
| HPMC | 48.0 |
| Cornstarch | 12.0 |
| Propylene glycol | 2.0 |

TABLE 11-continued

Red Film

| Ingredients | Wt. % |
| --- | --- |
| Tween 80 | 2.0 |
| Vegetable oil | 4.0 |
| Flavor | 24.0 |
| D&C #30 | 4.0 |
| Titanium oxide coated mica | 4.0 |
| Total | 100 |

EXAMPLE 17

This example illustrates a composition and method for the production of a blue dentifrice carrier material. To produce a blue dentifrice base a base formulation is prepared according to the method described in Example 14, except that a blue colorant is substituted for the blue colorant in table 10.

EXAMPLE 18

This example illustrates a composition comprising both a blue dentifrice carrier base formulation and a plurality of red heart, shaped film fragments, as well as a method of producing a composition.

To make the composition, red heart shaped film fragments of Example 16 are combined with blue dentifrice carrier material of Example 17, in a 0.3% (weight/weight) film: carrier ratio. Gentle mixing is used to distribute the film fragments throughout the base formulation. The composition is thereafter packaged in a standard toothpaste tube.

After packaging, a sample of the dentifrice composition is squeezed from a tube and is extruded as a distinctive blue, aesthetically pleasing ribbon composition having suspended therein clearly visible heart shaped red colored film fragments extending throughout the extruded composition.

EXAMPLE 19

This example illustrates a composition of circle-shaped film fragments comprising a high flavorant concentration and a method for their production.

A film having a high flavor concentration (23.75 wt. %) is prepared following the procedure of Example 13, except that a dry film comprising the ingredients listed in Table 12 was used. The dried film is then cut into and film fragments in the shape of circles.

TABLE 12

| Ingredients | Wt. % |
| --- | --- |
| HPMC | 48.0 |
| Cornstarch | 12.0 |
| Tween 80 | 2.0 |
| Propylene glycol | 2.0 |
| Canola oil | 4.0 |
| Flavor | 23.75 |
| Titanium coated mica | 8.0 |
| Sodium fluoride | 0.243 |
| Total | 100 |

EXAMPLE 20

This example illustrates the production of a composition that provides a flavor burst. In this example, a plurality of film fragments of Example 19 is combined with a dentifrice carrier of Example 14 according to the method of Example 15.

The resulting composition is tested through use in toothbrushing. When brushed on teeth, the composition emits a burst of flavor as the brushing cause the mechanical rupture of the film fragments with the immediate release of their flavor constituent.

EXAMPLE 20

This example illustrates film fragments comprising an oral care-effective amount of calcium and a method for their preparation. Film fragments of 2.5 microns thickness containing an oral care-effective amount of calcium are prepared according to the procedure disclosed in Example 13 except that the slurry comprised the ingredients listed in table 13 and the film fragments are not necessarily star shapes.

TABLE 13

| Ingredients | Wt. % |
| --- | --- |
| HPMC | 43.0 |
| Calcium acetate | 21.4 |
| Tween 80 | 1.8 |
| Propylene glycol | 1.8 |
| Canola oil | 3.5 |
| Flavor | 21.4 |
| Titanium coated mica | 7.1 |
| Total | 100 |

EXAMPLE 21

This example illustrates a composition comprising both a carrier comprising fluoride and a plurality of film fragments comprising calcium, as well as a method of making the composition. An analysis of some of composition's properties is also disclosed.

In this example, a composition comprising film fragments of Example 20 and a commercial fluoride toothpaste containing 1100 parts per million (ppm) fluoride ion is formed according to the method of Example 15. The composition comprises film fragments 0.3% by weight. This composition, designated "Paste A," is then aged at 120° F. for 2 to 8 weeks and analyzed for fluoride content at weekly intervals. For purposes of comparison, the same toothpaste but in which the film fragments had not been incorporated, designated "Paste B," is also analyzed for fluoride levels during the same intervals. The presence of fluoride ion in the compositions is determined by separating the carrier from the film fragments first then analyzing the carrier for the presence of fluoride using $F^-$ ion-selective electrodes.

The fluoride assays of the two compositions are shown in Table 14 below.

TABLE 14

| | Weeks | | | | |
| --- | --- | --- | --- | --- | --- |
| | 1 | 2 | 3 | 4 | 8 |
| Paste | $F^-$ (ppm) | $F^-$ (ppm) | $F^-$ (ppm) | $F^-$ (ppm) | $F^-$ (ppm) |
| A | 935 | 962 | 900 | 943 | 899 |
| B | 1016 | 1042 | 986 | 1036 | 1040 |

The results set forth in Table 14 show a minimal loss of fluoride ion over the 8-week assay period in Paste A comprising calcium acetate as compared to Paste B which did not contain any calcium salt. When brushed on teeth of the film suspended in the dentifrice will rapidly disintegrate whereby calcium ion will be released to interact with the fluoride ion to enhance the anticaries efficacy of the fluoride ion on the teeth being brushed.

EXAMPLE 22

This example illustrates film fragments comprising cetyl pyridinium chloride (CPC) and a method for their preparation. Film fragments of 2.5 microns thickness containing an oral care-effective amount of cetyl pyridinium chloride are prepared according to the procedure disclosed in Example 13 except that the dry film comprised the ingredients listed in table 15 below, and the film fragments are not necessarily star shapes. In Table 15 below lists ingredients of a film comprising CPC.

TABLE 15

| Ingredients | Wt. % |
| --- | --- |
| HPMC | 48.0 |
| CPC | 12.0 |
| Tween 80 | 2.0 |
| Propylene glycol | 2.0 |
| Canola oil | 4.0 |
| Flavor | 24.0 |
| Titanium coated mica | 8.0 |
| Total | 100 |

EXAMPLE 23

This example illustrates a composition comprising both a carrier comprising sodium lauryl sulfate (SLS) and plurality of film fragments comprising cetyl pyridinium chloride (CPC), as well as a method of producing a composition.

In this example, a plurality of film fragments of Example 22 are combined with an SLS-containing carrier, such as a dentifrice carrier as in Example 21 to produce a composition comprising both a carrier comprising sodium lauryl sulfate (SLS) and plurality of film fragments comprising cetyl pyridinium chloride (CPC). In the composition, the CPC will not react with the SLS present in the carrier. However, the CPC will be released during tooth brushing, and both the SLS and the CPC can be effective for oral hygiene.

EXAMPLE 24

This example illustrates, in table 16, a dosage of each of certain pharmaceuticals that can be delivered using a composition disclosed herein.

TABLE 16

| MEDICAMENT | DOSE |
| --- | --- |
| Chlorpheniramine Maleate | 4 mg. |
| Brompheniramine Maleate | 4 mg. |
| Dexchlorpheniramine | 2 mg. |
| Dexbrompheniramine | 2 mg. |
| Triprolidine Hydrochloride | 2.5 mg. |
| Acrivastine | 8 mg. |
| Azatadine Maleate | 1 mg. |
| Loratidine | 10 mg. |

TABLE 16-continued

| MEDICAMENT | DOSE |
| --- | --- |
| Phenylephrine Hydrochloride | 10 mg. |
| Dextromethorphan Hydrochloride | 10-20 mg. |
| Ketoprofen | 12.5 mg. |
| Sumatriptan Succinate | 35-70 mg. |
| Zolmitriptan | 2.5 mg. |
| Loperamide | 2 mg. |
| Famotidine | 10 mg. |
| Nicotine | 2 mg. |
| Diphenhydramine Hydrochloride | 25 mg. |
| Pseudoephedrine Hydrochloride | 30 mg. |

The examples and other embodiments described herein are exemplary and not intended to be limiting in describing the full scope of compositions and methods of this invention. Equivalent changes, modifications and variations of specific embodiments, materials, compositions and methods may be made within the scope of the present invention, with substantially similar results.

What is claimed is:

1. A dentifrice comprising an acceptable carrier suitable for use in a dentifrice having distributed therein a plurality of film fragments having an aspect ratio of at least about 5:1;
   wherein said film fragments comprise a matrix and a functional material;
   wherein said matrix comprises a water soluble material which comprises hydroxypropylmethylcellulose; and
   wherein said film fragments comprise a controlled release composition comprising said functional material and said film has a Dissolution Value of at least about 5 seconds and not more than about 200 seconds.

2. A dentifrice comprising a plurality of film fragments in a carrier, wherein said carrier is suitable for use in a dentifrice, and wherein said film fragments are visibly discernable, have either or both of a non-random shape or a repeating shape and are comprised of a film matrix, wherein the matrix comprises a water soluble material which comprises a hydroxypropylmethylcellulose;
   wherein said film fragments comprise a plurality of first film fragments having one or more of a first therapeutic active, a first dissolution rate, a first shape and a first color, and a plurality of second film fragments having one or more of a second therapeutic active, a second dissolution rate, a second shape and a second color.

3. A dentifrice comprising a plurality of film fragments in a carrier, wherein said carrier is suitable for use in a dentifrice, and wherein said film fragments are visibly discernable, have either or both of a non-random shape or a repeating shape and are comprised of a film matrix, wherein the matrix comprises a water soluble material which comprises a hydroxypropylmethylcellulose;
   wherein said film fragments comprise a controlled release composition comprising a functional material and said film fragments have a Dissolution Value of at least about 5 seconds and not more than about 200 seconds.

4. A dentifrice comprising a plurality of film fragments in a carrier, wherein said carrier is suitable for use in a dentifrice, and wherein said film fragments are visibly discernable, have either or both of a non-random shape or a repeating shape and are comprised of a film matrix, wherein the matrix comprises a water soluble material which comprises a hydroxypropylmethylcellulose;
   wherein said film fragments comprise a plurality of layers, and wherein said film fragments comprise a coating on at least one surface of said film fragments.

5. The dentrifice according to claim 1, wherein said functional material comprises a therapeutic active which provides a systemic health benefit.

6. A dentifrice comprising an acceptable carrier suitable for use in a dentifrice having distributed therein a plurality of film fragments having an aspect ratio of at least about 5:1,
- wherein said film fragments comprise a matrix and a functional material;
- wherein said matrix comprises a water soluble material which comprises a hydroxypropylmethylcellulose;
- wherein the film fragments comprise a plurality of first film fragments having one or more of a first therapeutic active, a first dissolution rate, a first shape and a first color, and a plurality of second film fragments having one or more of a second therapeutic active, a second dissolution rate, a second shape and a second color;
- wherein said first and second film fragments are substantially lamellar, having a thickness of about 0.1 mils to about 10 mils and a length of at least about 0.2 mm and not more than about 2.5 mm; and
- wherein said film fragments comprise a controlled release composition comprising said functional material and said film fragments have a Dissolution Value of at least about 5 seconds and not more than about 200 seconds.

* * * * *